United States Patent
Owen et al.

(10) Patent No.: US 8,431,523 B2
(45) Date of Patent: *Apr. 30, 2013

(54) OLIGOMERIC BIOSURFACTANTS IN DERMATOCOSMETIC COMPOSITIONS

(76) Inventors: Donald R. Owen, Madisonville, LA (US); Lili Fan, Kenner, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/995,049

(22) PCT Filed: May 29, 2009

(86) PCT No.: PCT/US2009/045616
§ 371 (c)(1),
(2), (4) Date: Nov. 29, 2010

(87) PCT Pub. No.: WO2009/148947
PCT Pub. Date: Dec. 10, 2009

(65) Prior Publication Data
US 2011/0250153 A1    Oct. 13, 2011

Related U.S. Application Data

(63) Continuation-in-part of application No. 12/227,825, filed as application No. PCT/US2007/012799 on May 31, 2007.

(60) Provisional application No. 61/071,985, filed on May 29, 2008, provisional application No. 60/809,825, filed on Jun. 1, 2006.

(51) Int. Cl.
*A61K 38/00* (2006.01)
*A61K 8/00* (2006.01)

(52) U.S. Cl.
USPC .............................................. 514/1.1; 424/59

(58) Field of Classification Search ........................ None
See application file for complete search history.

(56) References Cited

U.S. PATENT DOCUMENTS

| | | | |
|---|---|---|---|
| 8,318,678 B2 * | 11/2012 | Marini | 514/20.7 |
| 2010/0029574 A1 * | 2/2010 | Marini | 514/17 |
| 2010/0144643 A1 * | 6/2010 | Owen et al. | 514/15 |

FOREIGN PATENT DOCUMENTS

| | | | |
|---|---|---|---|
| WO | WO 2007143006 | * | 12/2007 |
| WO | WO 2009148551 | * | 12/2009 |

* cited by examiner

*Primary Examiner* — Marcela M Cordero Garcia
(74) *Attorney, Agent, or Firm* — Louis C. Paul

(57) ABSTRACT

Oligomeric acylated biosurfactants ("OABs") having low critical micelle concentrations of from about 1.0 ppm to about 200 ppm, preferably less than about 50 ppm, in an aqueous solution of Minimal Essential Media that can lower the surface tension in the aqueous MEM environment to less than about 50 dynes/cm$^2$ and have the ability to increase metabolic soluble proteins and/or increase synthesis of extracellular skin matrix proteins and/or increase rates of cell turnover while at the same time exhibiting comparatively low toxicity—preferably, an LD$_{50}$ of greater 200 ppm in 37 year-old female fibroblast cells. Another aspect of the present invention is directed to the use of OABs in formulations that are topically-applied, by which is meant the formulation is placed in direct contact with the skin, hair and nails as well as mucosa of the eyes, ears, nose, mouth, anus and vagina.

5 Claims, No Drawings

OLIGOMERIC BIOSURFACTANTS IN DERMATOCOSMETIC COMPOSITIONS

CROSS-REFERENCE TO RELATED APPLICATIONS

This application is the U.S. National Phase Application under 35 U.S.C. §371 of International Patent Application No. PCT/US2009/045616 filed 29 May 2009, claims priority to U.S. Provisional Application Ser. No. 61/071,985 filed on May 29, 2008, which is also a continuation-in-part of U.S. patent application Ser. No. 12/227,825, a U.S. national phase application filed under 35 U.S.C. §371 on Nov. 28, 2008. U.S. patent application Ser. No. 12/227,825 is based on international application PCT/US2007/012799, which was filed on May 31, 2007. U.S. patent application Ser. No. 12/227,825 and PCT/US2007/012799 both claim priority to U.S. Provisional Application Ser. No. 60/809,825 filed Jun. 1, 2006. The disclosures of International Patent Application No. PCT/US2009/045616, U.S. Application Ser. Nos. 61/071,985, 60/809,825 and 12/227,825 and PCT/US2007/012799 are incorporated herein by reference in their entirety. The International Application was published as WO 2009/148947 in the English language on 10 Dec. 2009.

FIELD OF INVENTION

The present invention is directed to biosurfactants that can self-assemble or auto-aggregate into oligomeric micellar structures and their use in topically-applied dermatologic products. The invention relates in particular to oligomeric acylated biosurfactants ("OABs") having low critical micelle concentrations ("CMC") of from about 1.0 ppm to about 200 ppm, preferably less than about 50 ppm, in an aqueous solution of Minimal Essential Media that can lower the surface tension in the aqueous MEM environment to less than about 50 dynes/cm$^2$ and have the ability to increase metabolic soluble proteins and/or increase synthesis of extracellular skin matrix proteins and/or increase rates of cell turnover while at the same time exhibiting comparatively low toxicity—preferably, an $LD_{50}$ of greater 200 ppm in 37 year-old female fibroblast cells. Another aspect of the present invention is directed to the use of OABs in formulations that are topically-applied, by which is meant the formulation is placed in direct contact with the skin, hair and nails as well as mucosa of the eyes, ears, nose, mouth, anus and vagina.

BACKGROUND OF THE INVENTION

PCT/US2007/012799, published as International Patent Application WO/2007/143006, describes the use of OABs having low critical micelle concentrations (predominantly less than about 100 ppm) in an aqueous environment of Minimal Essential Media (MEM) that (i) can lower the surface tension in the aqueous MEM environment to less than about 50 dynes/cm$^2$ and (ii) have the ability to increase metabolic soluble proteins. Creams, lotions, gels and serums comprising specific OABs, each having different properties, are disclosed. Among the properties of the OABs disclosed in WO/2007/143006 are the ability to increase the synthesis of skin matrix proteins (e.g., elastin, fibronectin, collagen) and/or increase cell turnover rates while not causing a concomitant increase in the synthesis of enzymes that degrade these proteins (e.g., matrix metalloproteinases). Additionally, several of the disclosed OABs are taught (i) not to cause an increase in inflammatory proteins (notably interleukin 6 and interleukin 8) and/or (ii) to have broad spectrum antimicrobial activity (i.e., the ability to inhibit the growth or kill a variety of microorganisms).

As discussed in WO/2007/143006, the use of amino acid sequences, both acylated and non-acylated, in topically-applied prescription and non-medicated (i.e., cosmeceutical) products skin care products is known in the art. Some such sequences are commercially-available as acylated moieties (e.g., acetyl, myristoyl, palmitoyl). In general, acylation is a well-known technique to those of skill in the art for enhancing penetration of a water-loving or hydrophilic ingredient into the skin. The surface of normal skin is highly hydrophobic preventing significant penetration by hydrophilic substances. However, the properties of an acylated amino acid sequence can vary greatly in terms of toxicity, which, in turn, affects its ultimate usefulness. Surprisingly and unexpectedly, many of the oligomeric acylated biosurfactants of the present invention have comparatively low toxicity to mammalian cells (on the order of $LD_{50}$>200) while at the same time maintaining a relatively high degree of toxicity for prokaryotic life forms.

Unlike prior art acylated amino acid sequences used in topically-applied products, OABs of the present invention have the ability to increase the synthesis of skin Essential Media (MEM) that (i) can lower the surface tension in the aqueous MEM environment to less than about 50 dynes/cm$^2$ and (ii) have the ability to increase metabolic soluble proteins. Creams, lotions, gels and serums comprising specific OABs, each having different properties, are disclosed. Among the properties of the OABs disclosed in WO/2007/143006 are the ability to increase the synthesis of skin matrix proteins (e.g., elastin, fibronectin, collagen) and/or increase cell turnover rates while not causing a concomitant increase in the synthesis of enzymes that degrade these proteins (e.g., matrix metalloproteinases). Additionally, surprisingly and significantly, OABs of the present invention do not cause an increase in inflammatory proteins, notably interleukin 6 and interleukin 8. This combination of properties makes these compounds uniquely suited to skin care applications.

The ability of OABs of the present invention to effectively wet surfaces at low CMCs confers another surprising and unexpected property—broad spectrum antimicrobial activity. Oligomeric biosurfactants of the present invention have the ability to inhibit the growth or kill a variety of microorganisms, including *Escherichia coli* (*E. coli*), *Pseudomonas aeruginosa* (*P. aeruginosa*), *Pseudomonas cepacia* (*P. cepacia*), *Staphylococcus aureus* (*S. aureus*), including methicillin resistant *S. aureus* (MRSA), including (ATCC BAA-41; ATCC BAA-44; ATCC-BAA-39), *Staphylococcus epidermidis* (*S. epidermidis*), and *Candida albicans* (*C. albicans*).

The International Search Report for WO/2007/143006 identified five prior art references, four patent references (i) WO 2004/099237 ("Ziegler"); (ii) US Patent Application Publication No. 2004/0229808 ("Owen"); (iii) US Patent Application Publication No. 2005/0142081 ("Breton") and (iv) US Patent Application Publication No. 2002/0111309 ("Castillo") and one non-patent article Brown, "Biosurfactants for cosmetic applications" Intl. J. Cosmet. Sci. Vol. 13, No. 2, pp. 61-64 ("Brown"). (Granted US patents and published US patent applications referenced herein are, to the extent pertinent, incorporated by reference.)

The Ziegler WO application teaches the use of specific acylated tripeptide sequences, including Lys-Val-Lys (KVK), Lys-Thr-Lys (KTK), Lys-Val-Arg (KVR), Lys-Leu-Lys (KLK), Lys-Ile-Lys (KIK), Lys-Ala-Lys (KAK), Lys-Ser-Lys (KSK), and Arg-Val-Arg (RVR).

The Breton US application teaches compositions comprising an N-acylaminoamide elastase inhibitor and at least one metalloproteinase inhibitor including adapalene or analogous peptides.

The Owen WO application is now U.S. Pat. No. 7,354,903 and is a continuation of U.S. patent application Ser. No. 09/820,053 filed Mar. 28, 2001, now U.S. Pat. No. 6,875,744. As discussed at Paragraph [0087] of WO/2007/143006, OAGs of the present invention are different from the "FLAK" peptides (i.e., those containing Phenylalanine, Leucine, Alanine, and Lysine residues) described in U.S. Pat. No. 6,875,744 which do not auto-aggregate in solution.

The Castillo US application discloses a method for treating diseases associated with beta-amyloid protein formation, deposition or accumulation, including Alzheimer's disease and Down's syndrome, with one of ten laminin-derived non-acylated polypeptides. Intravenous application is taught to be preferred; however, topical, intraarterial, intraperitoneal, oral, intralymphatic, intramuscular and intralumbar administration are also disclosed. The ISR specifically notes the polypeptides of SEQ ID NO 5 which is comprised of 3,075 amino acid residues. Of the remaining sequences, SEQ ID NO 1 is the shortest—containing 11 amino acids. The next shortest of the remaining disclosed sequences contains more than one hundred amino acid residues. OAGs of the present invention are from three to nine amino acids in length.

The Brown article discloses biosurfactants produced by microorganisms, including species of *Bacillus, Penicillium* and *Cornybacterium*. The OAGs of the present invention are short sequences of amino acids, from three to nine residues in length, that are made synthetically.

International Patent Application Publication WO/2007/093839 discloses polypeptides according to the formula: A-(Xaa)$_n$-Lys-X-Lys-B. A is defined as —NH2, NH3+, or NH-D, where D is an acyl group, either biotin or alkyl C$_2$-C$_{22}$. B is defined as H, O_OR$_1$, or NR$_2$R$_3$, where R$_1$, R$_2$ and R$_3$ are independently either H or an alkyl chain (C$_1$-C$_{24}$). (Xaa)$_n$ is an amino acid chain including any natural or synthetic amino acid, but excluding arginine and lysine, where n is an integer between 0 and 3. X is defined as a chain of two amino acids (Xaa$_1$Xaa$_2$), which may be the same or different, excluding arginine, lysine and excluding Xaa$_1$Xaa$_2$=Thr-Thr, Gly-His and Glu-His, or X is a spacer selected among beta-alanyl (β-Ala), 5-amino-valeroyl ("Ava"), 4-amino-cyclohexanoyl, 4-amino-butyroyl ("Abu"), 6-amino-caproyl ("Aca") and derivatives thereof. More particularly, WO/2007/093839 discloses acylated tetrapeptides according to the formula A-Lys-Xaa$_1$Xaa$_2$-Lys-B, where neither Xaa nor Xaa$_2$ are Arg or Lys. Also excluded from this formula are the tetrapeptide sequences: Lys-Thr-Thr-Lys; Lys-Gly-His-Lys; and Lys-Glu-His-Lys. The following tetrapeptide sequences acylated with a palmitoyl ("Pal") or elaidoyl ("Ela") moiety are specifically disclosed: Pal-Lys-Thr-Phe-Lys; Ela-Lys-Thr-Phe-Lys; Ela-Lys-Thr-Ala-Lys; Pal-Lys-Ava-Lys; Ela-Lys-Ala-Tyr-Lys; Ela-Lys-Phe-Tyr-Lys; Pal-Lys-R-Ala-Lys; Pal-Lys-Abu-Lys; and Pal-Lys-Aca-Lys. The International Search Report issued for WO/2007/093839 cites two prior art references, both of which teach the tetrapeptide sequence Lys-Thr-Phe-Lys ("KTFK").

One aspect of the present invention is directed to hair care compositions comprising OABs and use of OABs in topically-applied prescription and cosmeceutical products to inhibit or reduce hair loss, to stimulate hair growth, and/or to create the appearance of a healthier, shinier, and/or fuller hair shaft and/or reduce the appearance of thinning hair. This application of OABs of the present invention is not claimed or suggested in WO/2007/143006.

Certain OABs disclosed in WO/2007/143006 having at least two charged amino acid residues have now been found to increase the expression of genes associated with cell proliferation and differentiation—KRT1, KRT14, FGF2, GRN and DEFB1. Without wishing to be bound by a theory, Applicants believe that this surprising and unexpected property contributes, in part, to the ability of OABs of the present invention to help to inhibit or reduce hair loss, to stimulate hair growth, and/or to create the appearance of a healthier, shinier, and/or fuller hair shaft and/or reduce the appearance of thinning hair.

The scientific and patent literature has reported that topical use of peptides stimulates hair growth. A subsection of the Background of Invention in WO/2007/143006 is entitled "Prior Art Amino Acid Sequences Used in Skin Care Products." Among the prior art references discussed is US Patent Application Publication No. 2006/0067905 which describes a method for treating hair loss by administering oleanolic acid, apigenin and Biotinyl-Gly-His-Lys. Biotinyl tripeptide is formed by grafting vitamin H (biotin) on the tripeptide Gly-His-Lys. As explained in WO/2007/143006, the biotinyl moiety on this compound does not confer sufficient hydrophobicity to produce biosurfactant properties.

International Patent Appln PCT/JP2005/004033 (published as WO/2005/082395) teaches the use of the hexapeptide RPLKPW (Arg-Pro-Leu-Lys-Pro-Trp) to promote hair growth and inhibit hair loss.

International Patent Application PCT/KR2006/004352 (published as WO/2007/049905) teaches the use of a thymosin beta-4 mimicking octapeptide KLKLTETG (Lys-Leu-Lys-Leu-Thr-Glu-Thr-Gln) for promoting hair growth.

U.S. Pat. No. 5,538,945 assigned to Procyte Corp. teaches the topical administration of copper-peptide complexes to stimulate hair growth, particularly in persons having androgenetic alopecia, alopecia greata, female pattern baldness and secondary alopecia. The disclosed copper-peptide complexes conform to the formula [R$_1$—R$_2$—R$_3$]: copper(II), wherein R$_1$ is an amino acid or amino acid derivative; R$_2$ is histidine or arginine; and R$_3$ is at least one amino acid or amino acid derivative joined to R$_2$ by a peptide bond, with the proviso that R$_1$ is not glycyl, alanyl, seryl or valyl when R$_2$ is histidyl and R$_3$ is lysine, lysyl-prolyl-valyl-phenylalanyl-valine, lysyl-valyl-phenylalanylvaline, lysyl-tryptophan, or lysyl-(glycyl)1-2-tryptophan, and with the further proviso that R$_1$ is not lysyl when R$_2$ is histidyl and R$_3$ is glycine, glycyl-prolyl-valyl-phenylalanyl-valine, glycyl-valyl-phenylalanyl-valine, glycyltryptophan, or glycyl-(glycyl)1-2-tryptophan.

International Application PCT/US2003/035558 (published as WO/2004/043415) teaches the topical application of the copper-peptide complexes described in Paragraph [0008] in combination with Minoxidil (6-amino-1,2-dihydro-1-hydroxy-2-imino-4-piperidinopyrimidine).

The hexapeptide Arg-Pro-Leu-Lys-Pro-Trp (RPLKPW) has been reported to stimulate hair growth in shaved mice after feeding at a dose of 1 mg/kg for 2 weeks. Y. Masaaki, et al. "RPLKPW, a Designed Hypotensive Peptide Relaxes Artery and Stimulates Hair Growth via Angiotensin AT2 Receptor" J. Pept. Sci., Vol. 2004, pp. 99-102.

The present invention is directed to OABs not previously disclosed in WO/2007/143006 (SEQ ID NO 1-SEQ ID NO 96) as well as new uses of OABs disclosed in that application (SEQ ID NO 97-SEQ ID NO 129). These OABs are setout in the sequence listing in Paragraph [0019] and have a critical micelle concentration of less than about 200 ppm, preferably less than about 50 ppm) in an aqueous environment of Minimal Essential Media ("MEM") Solution (as defined below) that reduce the surface tension in the aqueous environment to less than about 50 dynes/cm$^2$. More particularly, the OABs consist essentially of (i) an 8- to 22-membered carbon chain, branched or unbranched, saturated or unsaturated, preferably myristoylated (abbreviated "Myr") or palmitoylated (abbreviated "Pal"); (ii) three to nine amino acid residues, at least one, preferably at least two of which is/are charged; and (iii) an acid C-terminus or an amide C-terminus.

As used in the present application, by charged amino acid is meant lysine, arginine, aspartic acid and glutamic acid.

Surprisingly, OABs of the present invention have been found to have an ability to increase metabolic soluble proteins by at least about 20% while exhibiting comparatively low toxicity for mammalian cells—preferably, having an $LD_{50}$ of greater 200 ppm in 37 year-old female fibroblast cells.

Also, surprisingly, many OABs of the present invention have the ability to increase synthesis and/or slow degradation of skin matrix proteins.

The following sequence listing forms part of the specification and is included to further illustrate certain aspects of the present invention. The invention maybe better understood by reference to one or more of these sequences in combination with the detailed description of the invention presented below.

| P # | Sequence | Sequence ID |
|---|---|---|
| P257 | Myr-GAR-acid | |
| P322 | Myr-AHR-amide | |
| P342 | Myr-RRR-amide | |
| P348 | Myr-KKK-acid | |
| P388 | Myr-DAD-acid | |
| P291 | Myr-KKAL-amide | SEQ ID NO 1 |
| P362 | Myr-KKAL-acid | SEQ ID NO 2 |
| P363 | Myr-LAKK-acid | SEQ ID NO 3 |
| P371 | Myr-IAKK-amide | SEQ ID NO 4 |
| P372 | Myr-LSKK-amide | SEQ ID NO 5 |
| P389 | Myr-DDAD-acid | SEQ ID NO 6 |
| P398 | Pal-AAKR-amide | SEQ ID NO 7 |
| P399 | Myr-GGKR-amide | SEQ ID NO 8 |
| P400 | Myr-AAKR-amide | SEQ ID NO 9 |
| P405 | Myr-KGL-[K]$^D$-amide | SEQ ID NO 10 |
| P190 | Myr-KTTKS-amide | SEQ ID NO 11 |
| P228 | Myr-TKTTK-amide | SEQ ID NO 12 |
| P263 | Pal-KKGEM-acid | SEQ ID NO 13 |
| P266 | Myr-GRKGD-acid | SEQ ID NO 14 |
| P293 | Myr-KKGEM-acid | SEQ ID NO 15 |
| P328 | Dod-KKALK-amide | SEQ ID NO 16 |
| P349 | Myr-KKALK-acid | SEQ ID NO 17 |
| P351 | Myr-KLAKK-acid | SEQ ID NO 18 |
| P361 | Myr-K-[K]$^D$-A-[L]$^D$-amide | SEQ ID NO 19 |
| P365 | Myr-KKLA-[K]$^D$-amide | SEQ ID NO 20 |
| P374 | Myr-KKGLK-amide | SEQ ID NO 21 |
| P382 | Myr-GRGDS-amide | SEQ ID NO 22 |
| P387 | Oct-GRGDS-amide | SEQ ID NO 23 |
| P390 | Myr-KKG1-[K]$^D$-amide | SEQ ID NO 24 |
| P394 | Myr-KKGL-[K]$^D$-amide | SEQ ID NO 25 |
| P395 | Myr-KKSL-[K]$^D$-amide | SEQ ID NO 26 |
| P401 | Myr-KIAK-[K]$^D$-amide | SEQ ID NO 27 |
| P414 | Myr-KLAK-[K]$^D$-amide | SEQ ID NO 28 |
| P418 | Myr-IIIKK-amide | SEQ ID NO 29 |
| P252 | Myr-KLAKKA-acid | SEQ ID NO 30 |
| P256 | Myr-AKKLAK-acid | SEQ ID NO 31 |
| P286 | Myr-d-[LKKALK]-acid | SEQ ID NO 32 |
| P296 | Myr-LKKALK-amide | SEQ ID NO 33 |
| P364 | Myr-PKKALK-amide | SEQ ID NO 34 |
| P396 | Myr-KLAKK-[L]$^D$-amide | SEQ ID NO 35 |
| P402 | Myr-AKKGL-[K]$^D$-amide | SEQ ID NO 36 |
| P404 | Myr-GKKAL-[K]$^D$-amide | SEQ ID NO 37 |
| P406 | Myr-LKKAL-[K]$^D$-acid | SEQ ID NO 38 |
| P408 | Myr-SKKAL-[K]$^D$-amide | SEQ ID NO 39 |
| P411 | Myr-DDSSKK-amide | SEQ ID NO 40 |
| P412 | Myr-DDLAKK-amide | SEQ ID NO 41 |
| P417 | Myr-IIIIIK-amide | SEQ ID NO 42 |
| P258 | Myr-AHR-acid | |
| P304 | Pal-GRK-amide | |
| P321 | Myr-KHR-amide | |
| P323 | Pal-AHR-amide | |
| P340 | Myr-KKK-amide | |
| P341 | Pal-KKK-amide | |
| P413 | Myr-SDD-acid | |
| P410 | Myr-DSDD-acid | SEQ ID NO 43 |
| P352 | Myr-d-[KKALK]-amide | SEQ ID NO 44 |
| P358 | Myr-[K]$^D$-KALK-amide | SEQ ID NO 45 |
| P378 | Myr-KKGIK-amide | SEQ ID NO 46 |
| P385 | Myr-KIAKK-amide | SEQ ID NO 47 |
| P409 | Myr-AGERA-acid | SEQ ID NO 48 |
| P295 | Myr-KLAKKL-amide | SEQ ID NO 49 |
| P355 | Myr-LKLAKK-amide | SEQ ID NO 50 |
| P403 | Myr-LKLAK-[K]$^D$-amide | SEQ ID NO 51 |
| P407 | Myr-AKKAL-[K]$^D$-amide | SEQ ID NO 52 |

| P # | Sequence | Sequence ID |
|---|---|---|
| P415 | Myr-KKKIII-amide | SEQ ID NO 53 |
| P397 | Pal-AARK-amide | SEQ ID NO 54 |
| P333 | Pal-KKLAK-amide | SEQ ID NO 55 |
| P380 | Myr-KKALKL-amide | SEQ ID NO 56 |
| P245 | Myr-GHR-amide | |
| P250 | Pal-GHR-amide | |
| P303 | Myr-GRK-amide | |
| P366 | Pal-G-H-[R]$^D$-amide | |
| P368 | Pal-KAKL-amide | SEQ ID NO 57 |
| P370 | Pal-LAKK-amide | SEQ ID NO 58 |
| P360 | Myr-[K]$^D$-K-[A]$^D$-L-[K]$^D$-amide | SEQ ID NO 59 |
| P373 | Myr-KKSLK-amide | SEQ ID NO 60 |
| P376 | Myr-LAIKK-amide | SEQ ID NO 61 |
| P369 | Myr-KKALKK-amide | SEQ ID NO 62 |
| P379 | Myr-KKALKA-amide | SEQ ID NO 63 |
| P381 | Myr-LKKALK-amide | SEQ ID NO 64 |
| P416 | Myr-IIIKKK-amide | SEQ ID NO 65 |
| P383 | Myr-SDGR-amide | SEQ ID NO 66 |
| P289 | Myr-LKAK-amide | SEQ ID NO 67 |
| P247 | Pal-VGVAPG-amide | SEQ ID NO 68 |
| P288 | Myr-KAKA-amide | SEQ ID NO 69 |
| P287 | Myr-AKAK-amide | SEQ ID NO 70 |
| P306 | Pal-GRKG-amide | SEQ ID NO 71 |
| P294 | Myr-GRKG-amide | SEQ ID NO 72 |
| P292 | Myr-LAKK-amide | SEQ ID NO 73 |
| P249 | Pal-GQPR-amide | SEQ ID NO 74 |
| P226 | Myr-KLAKK-amide | SEQ ID NO 75 |
| P261 | Pal-KLAKK-acid | SEQ ID NO 76 |
| P225 | Myr-KKGEM-amide | SEQ ID NO 77 |
| P216 | Myr-KRGKP-amide | SEQ ID NO 78 |
| P260 | Pal-KRGDR-acid | SEQ ID NO 79 |
| P214 | Myr-KKALK-amide | SEQ ID NO 80 |
| P329 | Pal-KKALK-amide | SEQ ID NO 81 |
| P262 | Pal-KKALK-acid | SEQ ID NO 82 |
| P215 | Myr-KKLAK-amide | SEQ ID NO 83 |
| P264 | Pal-GRKGD-acid | SEQ ID NO 84 |
| P222 | Myr-GRKGD-amide | SEQ ID NO 85 |
| P234 | Myr-KLAKKL-acid | SEQ ID NO 86 |
| P350 | Myr-AKKLAK-amide | SEQ ID NO 87 |
| P251 | Myr-AKKALK-acid | SEQ ID NO 88 |
| P230 | Myr-STKTTK-amide | SEQ ID NO 89 |
| P239 | Myr-SRVSRRSR-amide | SEQ ID NO 90 |
| P187 | Myr-LAKLAKKAF-amide | SEQ ID NO 91 |
| P189 | Myr-LAKKALKAF-acid | SEQ ID NO 92 |
| P285 | Myr-d-[KLAKKL]-acid | SEQ ID NO 93 |
| P243 | Myr-TKTSKS-amide | SEQ ID NO 94 |
| P238 | Myr-KRGDR-amide | SEQ ID NO 95 |
| P241 | Myr-KSSKS-amide | SEQ ID NO 96 |
| P242 | Myr-KTTK-amide | SEQ ID NO 97 |
| P359 | Myr-KKAL-d-[K]-amide | SEQ ID NO 98 |
| P235 | Myr-LKKALK-acid | SEQ ID NO 99 |
| P290 | Myr-KAKL-amide | SEQ ID NO 100 |
| P392 | Pal-R-amide | |
| P386 | Myr-DD-acid | |
| P391 | Myr-R-amide | |
| P316 | Pal-KK-amide | |
| P318 | Pal-RR-amide | |
| P393 | Myr-RH-amide | |
| P300 | Myr-GR-amide | |
| P315 | Myr-KK-amide | |
| P320 | Pal-HR-amide | |
| P347 | Myr-KK-acid | |
| P367 | Pal-K-[K]$^D$-amide | |
| P420 | Myr-III-amide | |

The amino acid sequences in OABs of the present invention can be made synthetically by techniques well-known to those of skill in the art, including solid state peptide synthesis as described, for example, in U.S. Pat. No. 6,620,419. (Granted US patents and published US patent applications referenced herein are, to the extent pertinent, incorporated by reference.) Unless otherwise noted, amino acids in the OABs are in L form. As will be appreciated by persons having ordinary skill in the art amino acids are commonly represented by one or three letter sequences:

| | | |
|---|---|---|
| A | Ala | Alanine |
| D | Asp | Aspartic Acid |
| E | Glu | Glutamic Acid |
| G | Gly | Glycine |
| H | His | Histidine |
| I | Ile | Isoleucine |
| K | Lys | Lysine |
| L | Leu | Leucine |
| M | Met | Methionine |
| R | Arg | Arginine |

| | | |
|---|---|---|
| P | Pro | Proline |
| S | Ser | Serine |
| T | Thr | Threonine |
| V | Val | Valine |

DETAILED DESCRIPTION OF THE INVENTION

The present invention is directed to oligomeric acylated biosurfactants ("OABs") having a critical micelle concentration of less than about 200 ppm, preferably less than about 50 ppm in an aqueous environment of MEM Solution, that reduce the surface tension of the MEM Solution to less than about 50 dynes/cm$^2$ where the OABs consist essentially of (i) an 8- to 22-membered carbon chain, branched or unbranched, saturated or unsaturated, preferably myristoylated; (ii) three to nine amino acid residues, at least one, preferably two, of which is charged; and (iii) an acid C-terminus or an amide C-terminus.

As used in the present application, "MEM Solution" is a 1,000 ml solution prepared by adding 10 grams of MEM Powder (as defined below) to 950 ml of deionized, distilled water at room temperature and mixing with gentle stirring. To this mixture is added 2.2 g of NaHCO$_3$ and 10 ml of Penicillin-Streptomycin Solution (as defined below). Deionized, distilled water is then added in a quantity sufficient to reach a final volume of 1,000 ml. The final pH of the MEM Solution is adjusted to 7.4-7.6 by slowly adding, with stirring, either 1 N NaOH or 1 N HCl. The MEM Solution is processed by membrane filtration through 0.2 µm filter using a positive pressure system. "MEM Powder", available from Invitrogen, Inc. (Carlsbad, Calif.) under the tradename GIBCO41500, contains the following ingredients at the listed concentrations:

| Ingredient | Concentration (mg/L) |
|---|---|
| Calcium Chloride (anhyd.) | 200.00 |
| Potassium Chloride | 40.00 |
| Magnesium Sulfate (anhyd.) | 97.67 |
| Sodium Chloride | 6800.00 |
| Sodium Phosphate-H$_2$O | 140.00 |
| D-Glucose | 1000.00 |
| Phenol Red | 10.00 |
| L-Alanine | 8.90 |
| L-Arginine-HCl | 126.00 |
| L-Asparagine-H2O | 15.00 |
| L-Aspartic Acid | 13.30 |
| L-Cystine-2HCl | 31.28 |
| L-Glutamic Acid | 14.70 |
| Glycine | 292.00 |
| L-Histidine-HCl—H$_2$O | 7.50 |
| L-Histidine | 42.00 |
| L-Isoleucine | 52.00 |
| L-Leucine | 52.00 |
| L-Lysine | 72.50 |
| L-Methionine | 15.00 |
| L-Phenylalanine | 32.00 |
| L-Proline | 11.50 |
| L-Serine | 10.50 |
| L-Threonine | 48.00 |
| L-Tryptophan | 10.00 |
| L-Tyrosine | 51.90 |
| L-Valine | 46.00 |
| D-Ca Pantothenate | 1.00 |
| Choline Chloride | 1.00 |
| Folic Acid | 1.00 |
| i-Inositol | 2.00 |
| Niacinamide | 1.00 |

| Ingredient | Concentration (mg/L) |
|---|---|
| Pyroxidal HCl | 1.00 |
| Riboflavin | 0.10 |
| Thiamine HCl | 1.00 |

"Penicillin-Streptomycin Solution" is a preparation consisting of 5,000 µg/ml Penicillin G sodium and 5,000 µg/ml Streptomycin sulfate in 0.85% saline and is also available from Invitrogen.

As used in the present application, by the term "biosurfactant" is meant a molecule having a charged hydrophilic head and long-chain carbon hydrophobic tail, preferably from about 8 to 22 carbon atoms in length. These molecules are described as biosurfactants because they auto-aggregate above their critical micelle concentration into oligomeric structures. In this respect, the compositions of the present invention maybe distinguished from the "FLAK" peptides (i.e., those containing Phenylalanine, Leucine, Alanine, and Lysine residues) as described in U.S. Pat. No. 6,875,744 which do not auto-aggregate in solution.

As used in the present application, by the term "acid C-terminus" is meant the functional group —COOH.

As used in the present application, by the term "amide C-terminus" is meant a functional group selected from —CONH$_2$, —CONHR, —CONR$_2$ where R is an alkyl, aryl or alkyl-aryl moiety.

For purposes of protecting the carboxy-terminal of the last amino acid of an amino acid sequence, an acid C-terminus or amide C-terminus, is preferably attached to the OAB. Processes for attaching protecting groups, esterification (—OR) and amidation (—NHR), are well-known to persons of skill in the art.

Acylation is a process well-known to those of skill in the art for protecting the N-terminus of an amino acid sequence to prevent further reactions with that group. Acyl functional groups have the formula R(C=O)—, where R is an organic group. They are formed by removal of the carboxylic hydroxyl group from an organic acid.

Methods for attaching acyl moieties at the N-terminus of an amino acid or amino acid sequence are well-known in the art. Among those known to those of skill in the art are the Friedel-Craft and Schotten-Baumann reactions, both using acyl chlorides. See e.g., U.S. Pat. No. 4,126,628, Japanese Patent No. JP 11140032, German Patent No. DE 19749556. See also Iyer, V. N., et al, J. Indian Chem. Soc. 59: 856-859 (1982); Paquet A. et al., Can. J. Chem. 60: 1806-1808 (1982).

Preferred acyl groups useful in the present invention have from 8 to 22-carbon atoms, branched or unbranched, saturated or unsaturated. More preferably, the acyl moiety is selected from the group consisting of myristoyl ("Myr") and palmitoyl ("Myr").

A first aspect of the present invention is directed to OABs having an ability to increase metabolic soluble proteins by at least about 20%. For purposes of the present invention, metabolic soluble protein is measured using the CBQCA Protein Quantitation Assay from Molecular Probes, Inc. (Eugene, Oreg.). This assay is based on aquinoline-2-carboxaldehyde derivative, which specifically reacts with primary amines to form conjugates capable of electrophoretic or chromatographic analysis. More specifically, in the presence of the cyanide anion, the quinoline-2-carboxaldehyde derivative reacts with primary amines, including those on proteins, and produces a highly-fluorescent emission at 550 nm. OABs meeting this criterion are selected from the group consisting of: Myr-GAR-acid (P257); Myr-GAR-acid (P322); Myr-RRR-amide (P342); Myr-KKK-acid (P348); Myr-DAD-acid (P388); SEQ ID NO 1 (P291); SEQ ID NO 2 (P362); SEQ ID NO 3 (P363); SEQ ID NO 4 (P371); SEQ ID NO 5 (P372); SEQ ID NO 6 (P389); SEQ ID NO 7 (P398); SEQ ID NO 8 (P399); SEQ ID NO 9 (P400); SEQ ID NO 11 (P190); SEQ ID NO 12 (P228); SEQ ID NO 13 (P263); SEQ ID NO 14 (P266); SEQ ID NO 15 (P293); SEQ ID NO 16 (P328) SEQ ID NO 17 (P349); SEQ ID NO 18 of 44 (P351); SEQ ID NO 19 (P361); SEQ ID NO 20 (P365); SEQ ID NO 21 (P374); SEQ ID NO 22 (P382); SEQ ID NO 23 (P387); SEQ ID NO 24 (P390); SEQ ID NO 25 (P394); SEQ ID NO 26 (P395); SEQ ID NO 27 (P401); SEQ ID NO 28 (P414); SEQ ID NO 29 (P418); SEQ ID NO 30 (P252); SEQ ID NO 31 (P256); SEQ ID NO 32 (P286); SEQ ID NO 33 (P296); SEQ ID NO 34 (P364); SEQ ID NO 35 (P396); SEQ ID NO 36 (P402); SEQ ID NO 37 (P404); SEQ ID NO 38 (P406); SEQ ID NO 39 (P408); SEQ ID NO 40 (P411); SEQ ID NO 41 (P412); SEQ ID NO 42 (P417); SEQ ID NO 54 (P397); SEQ ID NO 55 (P333); and SEQ ID NO 56 (P380).

One preferred embodiment within this first aspect is directed to OABs consisting essentially of three amino acid residues selected from the group consisting of: Myr-GAR-acid (P257); Myr-GAR-acid (P322); Myr-RRR-amide (P342); Myr-KKK-acid (P348); and Myr-DAD-acid (P388).

Another preferred embodiment within this first aspect is directed to OABs consisting essentially of four amino acid residues selected from the group consisting of: SEQ ID NO 1 (P291); SEQ ID NO 2 (P362); SEQ ID NO 3 (P363); SEQ ID NO 4 (P371); SEQ ID NO 5 (P372); SEQ ID NO 6 (P389); SEQ ID NO 7 (P398); SEQ ID NO 8 (P399); SEQ ID NO 9 (P400); SEQ ID NO 10 (P405); and SEQ ID NO 54 (P397).

A further preferred embodiment within this first aspect is directed to OABs consisting essentially of five amino acid residues selected from the group consisting of: SEQ ID NO 11 (P190); SEQ ID NO 12 (P228); SEQ ID NO 13 (P263); SEQ ID NO 14 (P266); SEQ ID NO 20 (P293); SEQ ID NO 16 (P328) SEQ ID NO 17 (P349); SEQ ID NO 18 (P351); SEQ ID NO 19 (P361); SEQ ID NO 20 (P365); SEQ ID NO 21 (P374); SEQ ID NO 22 (P382); SEQ ID NO 23 (P387); SEQ ID NO 24 (P390); SEQ ID NO 25 (P394); SEQ ID NO 26 (P395); SEQ ID NO 27 (P401); SEQ ID NO 28 (P414); SEQ ID NO 29 (P418); and SEQ ID NO 55 (P333).

A still further preferred embodiment within this first aspect is directed to OABs consisting essentially of six amino acid residues selected from the group consisting of: SEQ ID NO 30 (P252); SEQ ID NO 31 (P256); SEQ ID NO 32 (P286); SEQ ID NO 33 (P296); SEQ ID NO 34 (P364); SEQ ID NO 35 (P396); SEQ ID NO 36 (P402); SEQ ID NO 37 (P404); SEQ ID NO 38 (P406); SEQ ID NO 39 (P408); SEQ ID NO 40 (P411); SEQ ID NO 41 (P412); SEQ ID NO 42 (P417); and SEQ ID NO 56 (P380).

$LD_{50}$, the administered dose that results in the death of half or 50% of the test population of cells, is a commonly used measured of cytotoxicity. A second aspect of the present invention is directed to OABs according to the first aspect having a $LD_{50}$ of greater than 200 ppm in 37 year-old female fibroblast cells (ATCC CRL-2122) using the CellTiter Blue Assay (Promega Corp., Madison, Wis.). The Promega Cell-Titer Blue Assay is based on the indicator dye alamar blue (also known as resazurin), a redox indicator that produces a fluorescent colorimetric signal in response to cellular metabolic activity of cells. More particularly, the dye permeates both the cellular and nuclear membranes of cells and is metabolized both by mitochondria and cytoplasmic microsomes. When metabolized, the dye forms a fluorimetric species with an emission at 590 nm. By measuring the intensity of the fluorescence, cellular viability can be quantified. As will be appreciated by persons of skill in the art, other similar cytotoxicity assays, such as the Alamar Blue Assays available from Biosource International and Trek Diagnostic Systems, may also be used.

OABs according to this second aspect of the present invention having a LD50 of greater than about 200 ppm in 37 year-old female fibroblast cells (ATCC CRL-2122) using the CellTiter Blue Assay are selected from the group consisting of: Myr-GAR-acid (P257); Myr-KKK-acid (P348); Myr-DAD-acid (P388); SEQ ID NO 1 (P291); SEQ ID NO 2 (P362); SEQ ID NO 3 (P363); SEQ ID NO 4 (P371); SEQ ID NO 6 (P389); SEQ ID NO 7 (P398); SEQ ID NO 11 (P190); SEQ ID NO 12 (P228); SEQ ID NO 13 (P263); SEQ ID NO 14 (P266); SEQ ID NO 15 (P293); SEQ ID NO 16 (P328); SEQ ID NO 17 (P349); SEQ ID NO 18 (P351); SEQ ID NO 20 (P365); SEQ ID NO 21 (P374); SEQ ID NO 22 (P382); SEQ ID NO 23 (P387); SEQ ID NO 24 (P390); SEQ ID NO 25 (P394); SEQ ID NO 26 (P395); SEQ ID NO 27 (P401); SEQ ID NO 28 (P414); SEQ ID NO 29 (P418); SEQ ID NO 30 (P252); SEQ ID NO 31 (P256); SEQ ID NO 33 (P296); SEQ ID NO 34 (P364); SEQ ID NO 35 (P396); SEQ ID NO 36 (P402); SEQ ID NO 37 (P404); SEQ ID NO 38 (P406); SEQ ID NO 39 (P408); SEQ ID NO 40 (P411); SEQ ID NO 41 (P412); and SEQ ID NO 42 (P417).

Particularly preferred OABs according to this second aspect of the present invention have a $LD_{50}$ of greater than about 300 ppm in 37 year-old female fibroblast cells (ATCC CRL-2122) using the CellTiter Blue Assay and are selected from the group consisting of: Myr-GAR-acid (P257); Myr-KKK-acid (P348); Myr-DAD-acid (P388); SEQ ID NO 1 (P291); SEQ ID NO 2 (P362); SEQ ID NO 3 (P363); SEQ ID NO 4 (P371); SEQ ID NO 6 (P389); SEQ ID NO 11 (P190); SEQ ID NO 12 (P228); SEQ ID NO 15 (P293); SEQ ID NO 16 (P328); SEQ ID NO 17 (P349); SEQ ID NO 18 (P351); SEQ ID NO 20 (P365); SEQ ID NO 22 (P382); SEQ ID NO 23 (P387); SEQ ID NO 24 (P390); SEQ ID NO 25 (P394); SEQ ID NO 26 (P395); SEQ ID NO 27 (P401); SEQ ID NO 28 (P414); SEQ ID NO 29 (P418); SEQ ID NO 30 (P252); SEQ ID NO 31 (P256); SEQ ID NO 33 (P296); SEQ ID NO 34 (P364); SEQ ID NO 36 (P402); SEQ ID NO 37 (P404); SEQ ID NO 39 (P408); SEQ ID NO 40 (P411); SEQ ID NO 41 (P412); and SEQ ID NO 42 (P417).

Even more particularly preferred OABs according to this second aspect of the invention have a $LD_{50}$ of greater than about 500 ppm in 37 year-old female fibroblast cells (ATCC CRL-2122) using the CellTiter Blue Assay and are selected from the group consisting of: Myr-GAR-acid (P257); Myr-DAD-acid (P388); SEQ ID NO 4 (P371); SEQ ID NO 6 (P389); SEQ ID NO 15 (P293); SEQ ID NO 16 (P328); SEQ ID NO 20 (P365); SEQ ID NO 29 (P418); SEQ ID NO 40 (P411); SEQ ID NO 41 (P412); SEQ ID NO 42 (P417).

A third aspect of the present invention is directed to OABs according to the first aspect of the present invention that also increase fibroblast proliferation. For purposes of the present invention, proliferation is assessed using the Cyquant® Cell Proliferation Assay from Molecular Probes. This assay measures increased production of cellular nucleic acids that, in turn, results in increased binding of fluorescent dye. OABs meeting this criterion are selected from the group consisting of: Myr-GAR-acid (P257); Myr-GAR-acid (P322); Myr-RRR-amide (P342); Myr-KKK-acid (P348); Myr-DAD-acid (P388); SEQ ID NO 6 (P291); SEQ ID NO 2 (P362); SEQ ID NO 3 (P363); SEQ ID NO 4 (P371); SEQ ID NO 5 (P372); SEQ ID NO 6 (P389); SEQ ID NO 7 (P398); SEQ ID NO 8 (P399); SEQ ID NO 9 (P400); SEQ ID NO 10 (P405); SEQ ID NO 11 (P190); SEQ ID NO 12 (P228); SEQ ID NO 13

(P263); SEQ ID NO 14 (P266); SEQ ID NO 15 (P293); SEQ ID NO 16 (P328) SEQ ID NO 17 (P349); SEQ ID NO 18 (P351); SEQ ID NO 19 (P361); SEQ ID NO 21 (P374); SEQ ID NO 22 (P382); SEQ ID NO 23 (P387); SEQ ID NO 24 (P390); SEQ ID NO 25 (P394); SEQ ID NO 26 (P395); SEQ ID NO 27 (P401); SEQ ID NO 28 (P414); SEQ ID NO 29 (P418); SEQ ID NO 30 (P252); SEQ ID NO 31 (P256); SEQ ID NO 33 (P296); SEQ ID NO 35 (P396); SEQ ID NO 36 (P402); SEQ ID NO 37 (P404); SEQ ID NO 38 (P406); SEQ ID NO 39 (P408); SEQ ID NO 40 (P411); SEQ ID NO 41 (P412); SEQ ID NO 42 (P417); SEQ ID NO 54 (P397); SEQ ID NO 55 (P333); and SEQ ID NO 56 (P380).

Particularly preferred OABs according to this third aspect of the invention increase fibroblast proliferation by at least 20% according to the Cyquant® Cell Proliferation Assay and are selected from the group consisting of: Myr-GAR-acid (P257); Myr-GAR-acid (P322); Myr-RRR-amide (P342); Myr-KKK-acid (P348); Myr-DAD-acid (P388); SEQ ID NO 6 (P291); SEQ ID NO 6 (P389); SEQ ID NO 7 (P398); SEQ ID NO 8 (P399); SEQ ID NO 9 (P400); SEQ ID NO 10 (P405); SEQ ID NO 12 (P228); SEQ ID NO 14 (P266); SEQ ID NO 15 (P293); SEQ ID NO 16 (P328); SEQ ID NO 23 (P387); SEQ ID NO 24 (P390); SEQ ID NO 25 (P394); SEQ ID NO 26 (P395); SEQ ID NO 27 (P401); SEQ ID NO 28 (P414); SEQ ID NO 33 (P296); SEQ ID NO 35 (P396); SEQ ID NO 36 (P402); SEQ ID NO 37 (P404); SEQ ID NO 39 (P408); SEQ ID NO 40 (P411); SEQ ID NO 41 (P412); SEQ ID NO 54 (P397); SEQ ID NO 55 (P333); and SEQ ID NO 56 (P380).

A fourth aspect of the present invention is directed to OABs having an amide C-terminus. Without wishing to be bound to a theory, Applicants believe that OABs having a carboxyamide group at the end of the amino acid sequence are less likely to be labile to hydrolysis, especially at pH values less than physiological pH. Moreover, as discussed above, certain amide-terminated OABs have been found to have a high LD50 for mammalian cells (i.e., greater than about 300 ppm and greater than about 500 ppm).

A fifth aspect of the present invention is directed to OABs according to the first aspect of the invention having antimicrobial activity against at least one, preferably two, more preferably at least three microorganisms selected from the group consisting of E. coli, P. aeruginosa, P. cepacia, S. aureus, including MRSA, S. epidermidis, and C. albicans.

By "antimicrobial" activity is meant the ability to inhibit the growth of at least one microbial organism selected from the group consisting E. coli, P. aeruginosa, S. aureus and C. albicans, as confirmed by optical density measurement ("OD").

By "inhibition of growth" is meant reduction or absence of an increase greater than 5% in OD, a dimensionless measure of turbidity that is proportional to the amount of microbial cells present in a sample. For illustrative purposes, a OAB according to the present invention is added to a culture plate on which E. coli is present at a final concentration of about $5 \times 10^3$ cfu/ml. The plate is then incubated at about 37° C. for about 24 hours at which time the E. coli is resuspended by shaking, and OD is measured at about 600 nm. Thus, a reduction or absence of an increase greater than 5% in OD confirms the antimicrobial nature of the OAB with respect to E. coli.

Minimum inhibitory concentration ("MIC") is a method well-known to those of skill in the art for expressing antimicrobial activity. A compound to be tested is serially diluted into growth medium, inoculated with culture and then incubated. The MIC is the lowest dilution of compound that inhibits or prevents growth of the target microorganism.

As discussed in WO/2007/143006, the presence of multiple charged amino acid residues on a OAB confers desirable properties including antimicrobial activity. However, because of steric effects and other biological interactions, antimicrobial activity (as well as other properties) based on number of charged amino acid residues has proven to be unpredictable.

One preferred embodiment of this fifth aspect of the present invention is directed to OABs having a $MIC_{(E.\ coli)}$ of 100 ppm or less and selected from the group consisting of: Myr-GAR-acid (P322); Myr-RRR-amide (P342); Myr-KKK-acid (P348); SEQ ID NO 6 (P291); SEQ ID NO 2 (P362); SEQ ID NO 3 (P363); SEQ ID NO 4 (P371); SEQ ID NO 5 (P372); SEQ ID NO 7 (P398); SEQ ID NO 8 (P399); SEQ ID NO 9 (P400); SEQ ID NO 10 (P405); SEQ ID NO 11 (P190); SEQ ID NO 15 (P293); SEQ ID NO 16 (P328); SEQ ID NO 17 (P349); SEQ ID NO 18 (P351); SEQ ID NO 19 (P361); SEQ ID NO 20 (P365); SEQ ID NO 21 (P374); SEQ ID NO 24 (P390); SEQ ID NO 25 (P394); SEQ ID NO 26 (P395); SEQ ID NO 27 (P401); SEQ ID NO 29 (P418); SEQ ID NO 30 (P252); SEQ ID NO 31 (P256); SEQ ID NO 32 (P286); SEQ ID NO 33 (P296); SEQ ID NO 34 (P364); SEQ ID NO 35 (P396); SEQ ID NO 36 (P402); SEQ ID NO 37 (P404); SEQ ID NO 38 (P406); SEQ ID NO 39 (P408); SEQ ID NO 42 (P417). according to the present invention is added to a culture plate on which E. coli is present at a final concentration of about $5 \times 10^3$ cfu/ml. The plate is then incubated at about 37° C. for about 24 hours at which time the E. coli is resuspended by shaking, and OD is measured at about 600 nm. Thus, a reduction or absence of an increase greater than 5% in OD confirms the antimicrobial nature of the OAB with respect to E. coli.

Another preferred embodiment of this fifth aspect of the present invention is directed to OABs having a $MIC_{(S.\ aureus)}$ of 100 ppm or less and selected from the group consisting of: Myr-GAR-acid (P322); Myr-RRR-amide (P342); Myr-KKK-acid (P348); SEQ ID NO 6 (P291); SEQ ID NO 2 (P362); SEQ ID NO 3 (P363); SEQ ID NO 4 (P371); SEQ ID NO 5 (P372); SEQ ID NO 7 (P398); SEQ ID NO 8 (P399); SEQ ID NO 9 (P400); SEQ ID NO 10 (P405); SEQ ID NO 11 (P190); SEQ ID NO 14 (P266); SEQ ID NO 15 (P293); SEQ ID NO 17 (P349); SEQ ID NO 18 (P351); SEQ ID NO 19 (P361); SEQ ID NO 20 (P365); SEQ ID NO 21 (P374); SEQ ID NO 24 (P390); SEQ ID NO 25 (P394); SEQ ID NO 26 (P395); SEQ ID NO 27 (P401); SEQ ID NO 30 (P252); SEQ ID NO 31 (P256); SEQ ID NO 32 (P286); SEQ ID NO 33 (P296); SEQ ID NO 34 (P364); SEQ ID NO 35 (P396); SEQ ID NO 36 (P402); SEQ ID NO 37 (P404); SEQ ID NO 38 (P406); and SEQ ID NO 39 (P408).

Yet another preferred embodiment of this fifth aspect of the present invention is directed to OABs having a $MIC_{(P.\ cepacia)}$ of 100 ppm or less and selected from the group consisting of: Myr-GAR-acid (P322); Myr-RRR-amide (P342); Myr-KKK-acid (P348); SEQ ID NO 6 (P291); SEQ ID NO 2 (P362); SEQ ID NO 3 (P363); SEQ ID NO 4 (P371); SEQ ID NO 50 (P372); SEQ ID NO 7 (P398); SEQ ID NO 8 (P399); SEQ ID NO 9 (P400); SEQ ID NO 11 (P190); SEQ ID NO 16 (P328); SEQ ID NO 17 (P349); SEQ ID NO 18 (P351); SEQ ID NO 19 (P361); SEQ ID NO 20 (P365); SEQ ID NO 21 (P374); SEQ ID NO 24 (P390); SEQ ID NO 25 (P394); SEQ ID NO 26 (P395); SEQ ID NO 32 (P286); SEQ ID NO 33 (P296); SEQ ID NO 34 (P364); SEQ ID NO 35 (P396); SEQ ID NO 36 (P402); SEQ ID NO 37 (P404); and SEQ ID NO 39 (P408).

OABs of the present invention have surprisingly and unexpectedly low CMCs in an aqueous MEM environment—some at less than about 25 ppm. A sixth aspect of the present invention is directed to the following OABs according to the first aspect of the invention having a CMC in an aqueous MEM environment of less than about 25 ppm and selected from the group consisting of: Myr-GAR-acid (P322); Myr-RRR-amide (P342); Myr-KKK-acid (P348); SEQ ID NO 6 (P291); SEQ ID NO 2 (P362); SEQ ID NO 3 (P363); SEQ ID NO 12 (P228); SEQ ID NO 13 (P263); SEQ ID NO 14 (P266); SEQ ID NO 15 (P293); SEQ ID NO 18 (P351); SEQ ID NO 19 (P361); SEQ ID NO 20 (P365); SEQ ID NO 21 (P374); SEQ ID NO 30 (P252); SEQ ID NO 32 (P286); SEQ ID NO 33 (P296); and SEQ ID NO 34 (P364).

A seventh aspect of the present invention is directed to OABs according to the first aspect of the present invention that can inhibit the growth of P. acnes at a concentration of less than about 100 ppm. OABs meeting this criterion are selected from the group consisting of: Myr-GAR-acid (P322); Myr-RRR-amide (P342); Myr-KKK-acid (P348); SEQ ID NO 6 (P291); SEQ ID NO 2 (P362); SEQ ID NO 3 (P363); SEQ ID NO 4 (P371); SEQ ID NO 5 (P372); SEQ ID NO 7 (P398); SEQ ID NO 8 (P399); SEQ ID NO 9 (P400); SEQ ID NO 10 (P405); SEQ ID NO 16 (P328); SEQ ID NO 17 (P349); SEQ ID NO 18 (P351); SEQ ID NO 19 (P361); SEQ ID NO 20 (P365); SEQ ID NO 21 (P374); SEQ ID NO 24 (P390); SEQ ID NO 25 (P394); SEQ ID NO 26 (P395); SEQ ID NO 27 (P401); SEQ ID NO 28 (P414); SEQ ID NO 30 (P252); SEQ ID NO 32 (P286); SEQ ID NO 33 (P296); SEQ ID NO 34 (P364); SEQ ID NO 35 (P396); SEQ ID NO 36 (P402); SEQ ID NO 37 (P404); SEQ ID NO 38 (P406); and SEQ ID NO 39 (P408).

A eighth aspect of the present invention is directed to OABs according to the first aspect of the invention that in addition to increasing soluble protein and/or cell proliferation also increase the expression of one or more genes that code for collagen, elastin or fibronectin—COL1 (collagen), fibronectin (FN1) and elastin (ELN). Levels of gene expression can be measured using DNA microarrays and a variety of other techniques well-known to those of skill in the art. See, e.g., Perou et al., Nature (London) 06: 747-752 (2000).

A more preferred embodiment of this eighth aspect of the invention is directed to the OABs that cause at least a twenty percent increase of at least one, preferably at least two of COL1, ELN or FN1, that also down regulate expression of MMP1.

Biosurfactants can produce inflammatory responses, which can be manifested in increased expression of IL6 and IL8. A ninth aspect of the present invention is directed to OABs according to the first aspect of the invention that do not cause an increase in the expression of IL6 and IL8.

Chronic upregulation of inflammatory genes (e.g., IL6 and IL8) has been observed to be correlated with upregulation of apoptotic genes such as CASP 1. The significant up-regulation of the pro-inflammatory genes IL-6 and IL-8 and/or the apoptotic related genes such as caspase 1 (CASP1) is not desirable. Lyer, V. R. et al., Science 283: 83-87 (1999); Mathy-Hartert M et al., Inflamm Res. 52(3):111-8 (2003); Raqib et al., Infection and Immunity June 2002, pp 3199-3207. A tenth aspect of the present invention is directed to OABs according to the first aspect of the invention that do not cause an increase in expression of CASP1.

An eleventh aspect of the present invention is directed to oligomeric acylated biosurfactants consisting essentially of from three to nine amino acid residues, at least one preferably two of which amino acid residues are charged, where the OAB is not within the first aspect of the invention and increases fibroblast proliferation by at least 20% based on the Cyquant® Cell Proliferation Assay (Molecular Probes). OABs meeting this criterion are selected from the group consisting of: Myr-AHR-acid (P258); Pal-GRK-amide (P304); Myr-KHR-amide (P321); Pal-AHR-amide (P323); Myr-KKK-amide (P340); Pal-KKK-amide (P341); Myr-SDD-acid (P413); SEQ ID NO 43 (P410); SEQ ID NO 44 (P352); SEQ ID NO 45 (P358); SEQ ID NO 46 (P378); SEQ ID NO 47 (P385); SEQ ID NO 48 (P409); SEQ ID NO 49 (P295); SEQ ID NO 50 (P355); SEQ ID NO 51 (P403); SEQ ID NO 52 (P407); and SEQ ID NO 53 (P415).

A twelfth aspect of the present invention is directed to oligomeric acylated biosurfactants consisting essentially of two or one amino acid residues, at least one of which is charged, having an $LD_{50}$ of greater than 200 ppm in 37 year-old female fibroblast cells (ATCC CRL-2122) using the Cell-Titer Blue Assay that also (i) increase fibroblast proliferation by at least 20% based on the Cyquant® Cell Proliferation Assay and (ii) increase metabolic soluble proteins by at least about 20% based on the CBQCA Protein Quantitation Assay. OABs meeting this criterion are selected from the group consisting of Pal-R-amide (P392) and Myr-DD-acid (P386).

Another aspect of the present invention is directed to oligomeric acylated biosurfactants having a CMC of less than 200 ppm in an aqueous environment of MEM Solution that reduces the surface tension of the MEM Solution to less than about 50 dynes/cm² where the OAB consists essentially of two or one amino acid residues, at least one of which is charged and (i) increases fibroblast proliferation by at least about 30% based on the Cyquant® Cell Proliferation Assay and (ii) also increases metabolic soluble protein based on the CBQCA Protein Quantitation Assay. OABs meeting this criterion are selected from the group consisting of Myr-R-amide (P391); Pal-KK-amide (P316); Pal-RR-amide (P318) and Myr-RH-amide (P393).

Surprisingly and unexpectedly, Myr-III-amide, Myr-III-amide (P420)—an OAB having no charged amino acid residues—has been found to increase metabolic soluble proteins by at least about 20% based on the CBQCA Protein Quantitation Assay.

Also surprisingly and unexpectedly, Pal-VGVAPG-amide, SEQ ID NO 68 (P247)—another OAB having no charged amino acid residues—has been found to increase fibroblast proliferation by at least about 30% based on the Cyquant® CellProliferation Assay.

A further aspect of the present invention is directed to oligomeric acylated biosurfactants having a CMC of less than about 100 ppm in an aqueous environment of MEM Solution that reduces the surface tension of the MEM Solution to less than about 50 dynes/cm² where the OAB consists essentially of two to nine amino acid residues, at least one of which is charged, and has a MIC of less than 100 ppm for at least two of the following microorganisms: E. coli, P. aeruginosa, P. cepacia, S. aureus, including MRSA, S. epidermidis, and C. albicans. OABs meeting this criterion are selected from the group consisting of: Myr-GR-amide (P300); Myr-KK-amide (P315); Pal-HR-amide (P320); Myr-KK-acid (P347); SEQ ID NO 79 (P367); Myr-GHR-amide (P245); Pal-GHR-amide (P250); Myr-GRK-amide (P303); Pal-G-H—[R]$^D$-amide (P366); SEQ ID NO 84 (368); SEQ ID NO 58 (P370); SEQ ID NO 59 (P360); SEQ ID NO 60 (P373); SEQ ID NO 61 (P376); SEQ ID NO 62 (P369); SEQ ID NO 63 (P379); SEQ ID NO 64 (P381); SEQ ID NO 65 (P416); SEQ ID NO 66 (P383); and SEQ ID NO 67 (P289).

In preferred embodiment of this aspect of the invention, the OAB has a CMC of less than about 50 ppm and is selected from the group consisting of: Myr-KK-amide (P315); Pal-HR-amide (P320); Pal-GHR-amide (P250); Myr-GRK-amide (P303); Pal-G-H—[R]$^D$-amide (P366); SEQ ID NO 58 (P370); SEQ ID NO 59 (P360); SEQ ID NO 60 (P373); SEQ ID NO 61 (P376); SEQ ID NO 62 (P369); SEQ ID NO 63 (P379); and SEQ ID NO 64 (P381).

In an even more preferred embodiment of this aspect of the invention, the OAB has a CMC of less than about 25 ppm and is selected from the group consisting of: Myr-KK-amide (P315); Pal-GHR-amide (P250); Myr-GRK-amide (P303); Pal-G-H913 [R]$^P$-amide (P366); SEQ ID SEQ ID NO 58 (P370); SEQ ID NO 59 (P360); SEQ ID NO 60 (P373); SEQ ID NO 61 (P376); SEQ ID NO 62 (P369); SEQ ID NO 63 (P379); SEQ ID NO 64 (P381).

A still further aspect of the present invention is directed to dicationic or tricationic OABs according to the first aspect of the invention that are comprised of five amino acid residues conforming to the formula Acyl-Lys-Lys-Gly-aa$_n$-Term wherein n is 2 and aa$_n$ is an amino acid selected from the group consisting of Glu, Met, Ile, Lys, d-Lys, and Leu, Acyl is Myr or Pal and Term is acid or amide. OABs meeting this criterion are selected from the group consisting of: SEQ ID NO 77 (P225), SEQ ID NO 13 (P263), SEQ ID NO 15 (P293), SEQ ID NO 21 (P374), SEQ ID NO 46 (P378), SEQ ID NO 24 (P390), and SEQ ID NO 25 (P394).

Another aspect of the present invention is directed OABs according to the first aspect of the invention that are comprised of from four to six amino acid residues wherein the oligomeric biosurfactant is comprised of at least two cationic amino acid residues and conforms to the formula Acyl-aa$_r$-Lys-aa$_s$-Ala-Lys-Lys-aa$_t$-Term wherein: r is 0 or 1; aa$_r$ is Leu; s is 0 or 1; aa$_s$ is Ile or Leu; t is 0 or 1; and aa$_t$ is Ala or Leu; Acyl is Myr or Pal; and Term is amide or acid. OABs meeting this criterion are selected from the group consisting of: SEQ ID NO 75 (P226), SEQ ID NO 86 (P234), SEQ ID NO 30 (P252), SEQ ID NO 76 (P261), SEQ ID NO 93 (P285), SEQ ID NO 49 (P295), SEQ ID NO 18 (P351), SEQ ID NO 50 (P355), SEQ ID NO 47 (P385), SEQ ID NO 35 (P396), SEQ ID NO 27 (P401), and SEQ ID NO 28 (P414).

A further aspect of the present invention is directed to OABs according to the first aspect of the invention that are comprised of from four to six amino acid residues wherein the oligomeric biosurfactant is comprised of at least two lysinyl amino acid residues and conforms to the formula Acyl-aa$_x$-Leu-aa$_v$-Lys-Lys-aa$_y$-Term wherein: x is an integer from 0 to 2; aa$_x$ is an amino acid selected from the group consisting of Lys and Leu; y is 0 or 1; aa$_y$ is an amino acid selected from the group consisting of Ala and Ser; v is 0 or 1; aa$_v$ is an amino acid selected from the group consisting of Ala and Leu; Acyl is Myr or Pal; and Term is amide or acid.

Preferred OABs according to this aspect of the invention are selected from the group consisting of: SEQ ID NO 75 (P226), SEQ ID NO 86 (P234), SEQ ID NO 30 (P252), SEQ ID NO 76 (P261), SEQ ID NO 93 (P285), SEQ ID NO 49 (P295), SEQ ID NO 18 (P351), SEQ ID NO 50 (P355), SEQ ID NO 5 (P372), SEQ ID NO 35 (P396), and SEQ ID NO 28 (P414).

An still further aspect of the present invention is directed to OABs according to the first aspect of the invention that are comprised of from four to six amino acid residues wherein the oligomeric biosurfactant is comprised of at least two lysinyl amino acid residues, and conforms to the formula Acyl-aa$_p$-Lys-Lys-aa$_{ff}$-Leu-aa$_q$-Term, wherein: p is 0 or 1; aa$_p$ is an amino acid residue selected from the group of Ala, Gly, Leu and Pro; ff is 0 or 1; aa$_{ff}$ is an amino acid residue selected from the group of Ala or Gly; q is 0, 1 or 2; aa$_q$ is an amino acid residue selected from the group of Ala, Lys and Leu; Acyl is Myr or Pal; and Term is amide or acid. OABs meeting this criterion are selected from the group consisting of: SEQ ID NO 88 (P251), SEQ ID NO 32 (P286), SEQ ID NO 1 (P291), SEQ ID NO 81 (P329), SEQ ID NO 44 (P352), SEQ ID NO 45 (P358), SEQ ID NO 98 (P359), SEQ ID NO 59 (P360), SEQ ID NO 19 (P361), SEQ ID NO 2 (P362), SEQ ID NO 34 (P364), SEQ ID NO 62 (P369), SEQ ID NO 63 (P379), SEQ ID NO 56 (P380), SEQ ID NO 36 (P402), SEQ ID NO 37 (P404), and SEQ ID NO 52 (P407).

In one preferred embodiment of this aspect of the invention, the oligomeric biosurfactant is comprised of from five or six amino acid residues, of which three amino acid residues are lysinyl, and the oligomeric biosurfactant conforms to the formula Acyl-aa$_p$-Lys-Lys-Ala-Leu-Lys-aa$_q$-Term, wherein: p is 0 or 1; aa$_p$ is an amino acid residue selected from the group of Ala, Gly and Pro; q is 0 or 1; aa$_q$ is an amino acid residue selected from the group of Ala and Leu; with the proviso that p+q=1.

In a particularly preferred embodiment of this aspect of the invention, the oligomeric biosurfactant is comprised of from five or six amino acid residues, of which three of the amino acid residues are lysinyl, and the oligomeric biosurfactant conforms to the formula Acyl-Lys-Lys-Ala-Leu-Lys-aa$_q$-Term wherein: q is 0 or 1; and aa$_q$ is an amino acid residue selected from the group of Ala and Leu.

In yet another particularly preferred embodiment of this aspect of the invention, OABs according to the first aspect of the invention are comprised of from five amino acid residues, of which three of the amino acid residues are lysinyl, and the oligomeric biosurfactant conforms to the formula Acyl-Lys-Lys-Ala-Leu-Lys-Term.

Another aspect of the present invention is directed to OABs according to the first aspect of the invention that are comprised of from four to six amino acid residues, of which at least two of the amino acid residues are lysinyl, and the oligomeric biosurfactant conforms to the formula Acyl-aa$_f$-Lys-aa$_g$-Leu-Lys-aa$_h$-Term wherein: f is 0, 1 or 2; aa$_f$ is an amino acid selected from the group of Ala, Gly, Lys and Pro; g is 0 or 1; aa$_g$ is an amino acid selected from the group of Ala, Gly and Ser; h is 0 or 1; aa$_h$ is an amino acid selected from the group of Ala and Leu; Acyl is Myr or Pal; and Term is amide or acid. OABs meeting this criterion are selected from the group consisting of: SEQ ID NO 88 (P251), SEQ ID NO 82 (P262), SEQ ID NO 32 (P286), SEQ ID NO 81 (P329), SEQ ID NO 44 (P352), SEQ ID NO 45 (P358), SEQ ID NO 98 (P359), SEQ ID NO 59 (P360), SEQ ID NO 19 (P361), SEQ ID NO 34 (P364), SEQ ID NO 62 (P369), SEQ ID NO 60 (P373), SEQ ID NO 63 (P379), SEQ ID NO 56 (P380), SEQ ID NO 26 (P395), SEQ ID NO 36 (P402), SEQ ID NO 37 (P404), SEQ ID NO 10 (P405), and SEQ ID NO 52 (P407).

Another aspect of the present invention is directed to OABs according to the first aspect of the invention that are comprised of five or six amino acid residues, of which three of the amino acid residues are lysinyl, and the oligomeric conforms to the formula Acyl-aa$_d$-Lys-Lys-Leu-Ala-Lys-Term, wherein: d is 0 or 1; aa$_d$ is Ala; Acyl is Myr or Pal; and Term is amide or acid. OABs meeting this criterion are selected from the group consisting of: SEQ ID NO 83 (P215), SEQ ID NO 31 (P256), SEQ ID NO 55 (P333), SEQ ID NO 87 (P350), and SEQ ID NO 20 (P365).

A further aspect of the present invention is directed to OABs according to the first aspect of the invention that are comprised of four amino acid residues, of which two of the amino acid residues are lysinyl, and the oligomeric conforms to the formula Acyl-aa$_k$-Lys-Ala-Lys-aa$_k$-Term, wherein: k is 1 and aa$_k$ is selected from the group consisting of Ala and Leu; Acyl is Myr or Pal; and Term is amide or acid. OABs meeting this criterion are selected from the group consisting of: SEQ ID NO 70 (P287), SEQ ID NO 69 (P288), SEQ ID NO 100 (P290), and SEQ ID NO 57 (P368).

Yet another aspect of the present invention is directed to OABs according to the first aspect of the invention that are comprised of from three to six amino acid residues, of which two of the amino acids form a dicationic sequence selected from the group consisting of Arg-Lys and Lys-Arg, and at least one of the amino acids is Gly, and the at least one Gly is bonded to Arg or Lys, and the oligomeric biosurfactant conforms to the formula Acyl-aa$_m$-Lys-Arg-aa$_n$-Term or to the formula Acyl-aa$_m$-Arg-Lys-aa$_n$-Term wherein: m is 0 or 1; aa$_m$ is Gly; n is 0, 1 or 2; aa$_n$ is selected from the group consisting of Asp, Gly, Lys and Pro; Acyl is Myr or Pal; and Term is amide or acid.

In a preferred embodiment of this aspect of the present invention the oligomeric biosurfactant comprises an amino acid sequence selected from the group consisting of: SEQ ID NO 78 (P216), SEQ ID NO 85 (P222), SEQ ID NO 95 (P238), SEQ ID NO 79 (P260), SEQ ID NO 84 (P264), SEQ ID NO 14 (P266), SEQ ID NO 72 (P294), Myr-GRK-amide (P303), Pal-GRK-amide (P304), and SEQ ID NO 71 (P306).

A further aspect of the present invention is directed to OABs according to the first aspect of the invention that are comprised of from three to six amino acid residues, that conform to the formula Acyl-Gly-Arg-aa$_{dd}$-Term, wherein: dd is an integer from 1 to 4, and amino acids within the group aa$_{dd}$ are selected from the group consisting of Gly, Asp, Ser and Lys, with the proviso that at least one of the aa$_{dd}$ group of amino acid residues is charged and is selected from Lys and Asp; Acyl is octanoylated (abbreviated "Oct"), Myr or Pal; and Term is amide or acid. OABs meeting this criterion are selected from the group consisting of: SEQ ID NO 85 (P222), SEQ ID NO 84 (P264), SEQ ID NO 72 (P294), Myr-GRK-amide (P303), Pal-GRK-amide (P304), SEQ ID NO 71 (P306), SEQ ID NO 22 (P382), and SEQ ID NO 23 (P387).

Another aspect of the present invention is directed to OABs according to the first aspect of the invention that are comprised of from four to eight amino acid residues, of which two of the amino acids form a dicationic amino acid sequence Lys-Lys, and the oligomeric biosurfactant contains at least one non-charged amino acid sequence Leu-Ala and the oligomeric biosurfactant conforms to the formula Acyl-aa$_{pp}$-Leu-Ala-aa$_{qq}$-Lys-Lys-aa$_{rr}$-Term wherein: pp is 0, 1 or 2; aa$_{pp}$ is selected from the group consisting of Leu, Ala and Lys; qq is 0 or 1; aa$_{qq}$ is Ile; rr is an integer from 0 to 4; aa$_{rr}$ is selected from the group consisting of Leu, Ala, Lys and Phe; Acyl is Myr or Pal; and Term is amide or acid. OABs meeting this criterion are selected from the group consisting of: SEQ ID NO 91 (P187), SEQ ID NO 92 (P189), SEQ ID NO 1 (P291), SEQ ID NO 73 (P292), SEQ ID NO 3 (P363), SEQ ID NO 58 (P370), and SEQ ID NO 61 (P376).

A further aspect of the present invention is directed to OABs according to the first aspect of the invention that are comprised of from four to six amino acid residues, of which at least two of the amino acids are lysinyl, and the oligomeric biosurfactant contains at least one amino acid sequence Leu-Lys, and at least one Lys is bonded to Ala, and the oligomeric biosurfactant conforms to the formula Acyl-Leu-Lys-aa$_{ss}$-Lys wherein ss is 0, 1 or 2 aa$_{ss}$ is Ala, Lys, or Leu; Acyl is Myr or Pal; and Term is amide or acid. OABs meeting this criterion are selected from the group consisting of: SEQ ID NO 99 (P235), SEQ ID NO 67 (P289), SEQ ID NO 33 (P296), SEQ ID NO 64 (P381), SEQ ID NO 51 (P403), and SEQ ID NO 38 (P406).

A further aspect of the present invention is directed to OABs according to the first aspect of the invention that are comprised of from three to six amino acid residues, of which at least two of the amino acids are Asp, and the oligomeric biosurfactant contains at least Ala or Ser, and the oligomeric biosurfactant conforms to the formula Acyl-Asp-aa$_{tt}$-Asp-aa$_{vv}$ wherein: tt is 0 or 1; aa$_{tt}$ is Ala or Ser; vv is an integer from 0 to 4; aa$_{vv}$ is selected from the group consisting of Ala, Asp, Lys and Ser; Acyl is Myr or Pal; and Term is amide or acid. OABs meeting this criterion are selected from the group consisting of: Myr-DAD-acid (P388), SEQ ID NO 6 (P389), SEQ ID NO 43 (P410), SEQ ID NO 40 (P411), and SEQ ID NO 41 (P412).

A still further aspect of the present invention is directed to OABs according to the first aspect of the invention that are comprised of four amino acid residues, wherein: two of the amino acids form a dicationic sequence selected from the group consisting of Arg-Lys and Lys-Arg, two of the amino acids form the sequence Ala-Ala, at least one Ala is bonded to Arg or Lys; Acyl is Myr or Pal; Term is acid or amide; and the oligomeric biosurfactant is selected from the group consisting of Acyl-Ala-Ala-Lys-Arg-Term and Acyl-Ala-Ala-Arg-Lys-Term. OABs meeting this criterion are selected from the group consisting of: SEQ ID NO 54 (P397), SEQ ID NO 7 (P398) and SEQ ID NO 9 (P400).

Another aspect of the present invention is directed to OABs according to the first aspect of the invention that are that conform to the formula Acyl-aa$_{ww}$-Arg-Term, wherein: the oligomeric biosurfactant is monocationic and contains an arginyl residue; the arginyl residue is preceded by an amino acid sequence (aa$_{ww}$) selected from the group consisting of Ala-His, Gly-His and Gly-Ala, with the proviso Ala or His is bonded to an arginyl residue; Acyl is Myr or Pal; Term is acid or amide. OABs meeting this criterion are selected from the group consisting of: Myr-GHR-amide (P245), Pal-GHR-amide (P250), Myr-GAR-acid (P257), Myr-AHR-acid (P258), Myr-AHR-amide (P322), Pal-AHR-amide (P323), and Pal-G-H—[R]$^D$-amide (P366).

Another aspect of the present invention is directed to acylated, amide-terminated, oligomeric biosurfactants according to the first aspect of the present invention that are comprised of five or six amino acid residues, the residues being either Ile or Lys, wherein the oligomeric biosurfactants are comprised of at least three Ile residues and at least one Lys residue. In a preferred embodiment of this aspect of the invention, the acylated, amide-terminated, oligomeric biosurfactants are selected from the group consisting of SEQ ID NO 65 (P416), SEQ ID NO 42 (P417), and SEQ ID NO 29 (P418).

A further aspect of the present invention is directed to acylated, amide-terminated, oligomeric biosurfactants according to the first aspect of the present invention that are comprised of from four or six amino acid residues, wherein the oligomeric biosurfactants are comprised of an Ile residue and at least two N-terminus Lys residues, and the remaining, non-terminal residues are selected from the group consisting of Ile, Lys, and Ala. In a preferred embodiment of this aspect of the invention, the acylated, amide-terminated, oligomeric biosurfactants are selected from the group consisting of SEQ ID NO 4 (P371), SEQ ID NO 65 (P416), and SEQ ID NO 29 (P418).

Another aspect of the present invention is directed to topical therapeutic application of OABs in cosmeceutical products as well as in prescription products dispensed by dermatologists for the purpose of treating and/or preventing dermatologic or other health-related conditions, including reducing the appearance of aging. Compositions comprising at least one OAB of the present invention may be topically applied, by which is meant placed in contact with the skin, hair or nails, as well as the mucosae of the eyes, ears, nose, mouth, anus and/or vagina by rubbing, wiping or dabbing with the fingers, or by means of an implement, non-limiting examples of which include a sponge or sponge-tipped applicator, a swab (for example, a cotton-tipped swab), a pen optionally comprising a foam or sponge applicator, a brush, a wipe, a pad or towelette. Non-limiting examples of conditions that may be treated, improved or maintained by topical application of a formulation comprising one or more OABs within the scope of the present invention are: skin elasticity; skin firmness; skin moisture; skin dryness; pruritus; blotches; fine lines and wrinkles; lentigines; age spots; acne; rosacea; hyperpigmented skin; keratoses, including actinic keratoses; skin cancers including melanoma, basal cell carcinoma, squamous cell carcinoma; alopecia, including alopecia greata and androgenic alopecia; thinning hair; dermatoses, including atopic dermatitis, contact dermatitis and seborrheic dermatitis; inflammatory skin conditions, including erythema multiforme and psoriasis; edema; neoplastic skin conditions in which the affected cells have (i) reduced expression of genes that code for endoskeletal proteins (ii) increased expression of genes that code for proteinases that degrade basement membranes and/or (iii) increased expression of the gene(s) associated with telomerase activity; skin atrophy; wound healing; scars; striae; cellulite; scleroderma; warts; herpes simplex; dermatomycoses, including but not limited to, candidiasis, onychomycosis, tinea infections; malodor, including odor caused by periodontal, axillary and perigenital bacteria. Additionally, as described above, topical compositions comprising OABs of the present invention may be used in the topical treatment of health-related conditions described in Freed berg et al., Fitzpatrick's Dermatology in General Medicine (2008); Kerdel, et al., Dermatologic Therapeutics (2005), and in Hardman et al., Lazo et al. Goodman & Gilman's: The Pharmacological Basis of Therapeutics (11th Edition 2005).

OABs within the scope of the present invention may be formulated as a single-phase liquid carrier (e.g., aqueous dispersion or anhydrous composition), as well as two or three-phase emulsions (water-in-oil, oil-in-water, water-in-silicone, silicone-in-water, water-in-oil-in-water, or oil-in-water-in-oil). By the term "anhydrous" is meant that water is not intentionally added to the composition. By the term "single-phase" is meant that the composition exists as one homogeneous phase (such as an oil phase).

One aspect of the present invention is directed to cosmeceutical hair care preparations comprised of at least one OAB that are topically-applied to the skin or the hair of the head (i.e., scalp) or face (eyebrows, eyelashes, beard and mustache) to create the appearance of thicker hair and/or reduce the appearance of thinning hair. Hair is comprised of two portions—the shaft, the dead cornified structure protruding above the epidermis, and the follicle, the tube-like opening in the epidermis where the hair shaft develops and into which the sebaceous glands open. The bottom-most portion of the follicle, the bulb, contains the rapidly dividing undifferentiated hair matrix cells. These cells divide and move up the follicle, differentiating into either hair cells or inner epithelial sheath cells. Non-limiting examples of OABs of the present invention that may be used in hair care preparations include SEQ ID NO 80 (P214); SEQ ID NO 83 (P215); SEQ ID NO 85 (P222); SEQ ID NO 77 (P225); SEQ ID NO 75 (P226); SEQ ID NO 89 (P230); SEQ ID NO 86 (P234); SEQ ID NO 99 (P235); and SEQ ID NO 69 (P288). In a preferred embodiment of this aspect of the invention, the hair care preparation is comprised of one of the following OABs that have been found to produce an increase of greater than 50% in the expression of at least one gene selected from the group KRT1, KRT14, FGF2, GRN and DEFB1: SEQ ID NO 80 (P214); SEQ ID NO 85 (P222); SEQ ID NO 77 (P225); and SEQ ID NO 86 (P234).

Topical application of OABs of the present invention have been found to accelerate the rate of hair regrowth based on testing in a BALB/c model. BALB/c mice were anesthetized; the back of the mice were shaved with electric clippers and divided into two parts. 100 µl of a thickened aqueous dispersion (a saline thickened with hydroxyethylcellulose in a ratio of about 9:2) comprising 1,000 ppm of OABs of the present invention were applied to a 1 $cm^2$ patch of shaved skin on one side. As a control the same thickened aqueous dispersion not containing OABs of the present invention was applied to the other side. Photographs were taken over a period of 21 days. The rate of hair regrowth on the side to which the OAB formulation was applied was observed to be faster.

Hair care preparations comprising at least one OAB within the scope of the present invention may include one or more polymers listed as "hair fixatives" in the 10th Edition of the International Cosmetic Ingredient Dictionary and Handbook published by the Cosmetic, Toiletry and Fragrance Association (now the Personal Care Products Council) (2004) and/or described as "hair fixing polymers" in International Patent Application Publication No. WO 2007/010494. Among the hair fixing polymers, cationic and non-ionic polymers are preferred.

Hair care preparations comprising one or more OABs within the scope of the present invention may contain one or more hair conditioning agents known to persons having ordinary skill in the art to make the hair more manageable, to minimize "fly away" static charge, and/or to detangle the hair. Additionally, such hair care preparations may contain one or more: peptides and peptide derivatives as disclosed in Paragraph [0042] of US Patent Application Publication No. 2007/0264210 ("Robinson"); hair growth regulators as disclosed in Robinson ¶ [0052], among which panthenol and pantothenic acid, as well as their isomers, salts and derivatives are preferred, as well as 6-amino-1,2-dihydro-1-hydroxy-2-imino-4-piperidinopyrimidine (Minoxidil); non-vitamin antioxidants and free radical scavengers as disclosed in Robinson ¶[0051]; vitamins as disclosed in Robinson ¶[0041], among which Vitamin A compounds, and natural and/or synthetic analogs thereof, and Vitamin B3 and B5 are preferred, and retinol, retinyl palmitate and retinoic acid are particularly preferred; minerals, mineral complexes, salts and derivatives as disclosed in Robinson ¶[0053], among which zinc and calcium are preferred; sugar amines (including, but not limited to, N-acetyl-glucosamine), as disclosed in Robinson ¶ [0053]; anti-inflammatory agents as disclosed in Robinson ¶[0057]; phytosterols and/or plant hormones as disclosed in Robinson ¶[0054]; as well as other active ingredients in US Patent Application Publication No. 2007/0264210 and U.S. Pat. No. 6,492,326.

The 10th Edition of the International Cosmetic Ingredient Dictionary and Handbook describes a wide variety of non-limiting cosmetic and pharmaceutical ingredients that, optionally, are suitable for use in topically-applied formulations containing OABs according to the present invention. Examples of these ingredient classes include: peptides and peptide derivatives; vitamins; minerals; antioxidants and free-radical quenchers; abrasives; exfoliants and keratolytics including, preferably, hydroxyacids; absorbents; astringents; preservatives and biocides, including those described in Steinberg, Preservatives for Cosmetics (2nd Edition, 2006); antimicrobial agents, including topical antibiotics, non-limiting examples of which include bacitracin, neomycin, erythromycin, mupirocin (Bactroban®), clindamycin, and polymyxin B, vancomycin, benzoyl peroxide, and combinations thereof, biguanides, and acyl arginine alkyl esters and salts; skin bleaching and lightening agents; external analgesics; sunscreen actives (i.e., organic compounds that absorb ultraviolet radiation from 290 nm to 400 nm, inorganic compounds that scatter or block ultraviolet radiation); film formers and other polymeric materials that increase the substantivity of topical compositions to the skin; humectants; thickening agents; chelators, including EDTA and citric acid; moisturizers; pH adjusters; skin-conditioning agents; skin soothing and/or healing agents; anti-acne agents; and dermal penetration enhancers, including those described in E W Smith and H I Maibach, Percutaneous Penetration Enhancers (2nd Edition, 2005), among which dimethyl isosorbide, oleyl alcohol and oleic acid are preferred. The cosmetic and/or pharmaceutical ingredients disclosed in U.S. Pat. No. 6,974, 799 and US Patent Application Publication No. 2005/0142095, may also be used in formulations containing OABs according to the present invention. Film-forming polymers, thickening agents, particulate fillers and volatile solvents suitable for use in formulating products that are intended to be topically-applied to enhance the appearance of the eyes (e.g., mascaras, lash extenders, lash conditioners, eye liners, eyebrow pencils), the skin (e.g., creams, lotions, gels, serums, including makeups) and the lips (e.g., lipstick, lip gloss, lip liner) are well-known to persons having ordinary skill in the art and are described in U.S. Pat. Nos. 6,726,900 and 6,492,326.

Without wishing to be bound by a theory, Applicants believe that topical application of OABs of the present invention accelerate healing because OABs of the present invention have surprisingly been found to upregulate the expression of genes associated with the synthesis of β-defensins, a class of natural (i.e., indigenous) proteins having antimicrobial activity produced by keratinocytes and immune cells. Non-limiting examples of OABs according to the present invention that upregulate the expression of at least one of the following three β-defensins, DEFB4, DEFB1 and DEFB103 by at least 40% include: SEQ ID NO 80 (P214); SEQ ID NO 85 (P222); SEQ ID NO 77 (P225); and SEQ ID NO 86 (P234). Topically-applied compositions comprising at least one OAB of the present invention intended to promote healing of wounded skin (i.e., skin that has been abraded, torn, cut, incised, punctured, lacerated, burned or otherwise penetrated) may additionally contain hydrogen peroxide or enzymes which generate hydrogen peroxide (i.e., glucose oxidase/lactoperoxidase).

OABs according to the present invention may also be used in treating and/or preventing infections caused by bilipid envelope viruses including the following: DNA virus infections (including but not limited to infections caused by Herpesviridae, Papillomavirus, Parvoviridae, Polyomavirus); RNA virus infections; AIDS-related opportunistic infections; superinfection; viral pneumonia; sexually-transmitted diseases; viral eye infections.

EXAMPLES

The following examples are further illustrative of the present invention. The components and specific ingredients are presented as being typical, and various modifications can be derived in view of the foregoing disclosure within the scope of the invention. Unless otherwise noted, percentages are by weight of the total composition.

Example 1

Nanoparticulate Concentrate

| Phase A | |
|---|---|
| DI Water | 70-90% |
| Phase B | |
| Medium chain triglyceride (C6-C12) | 2-8% |
| Lecithin 2-8 % Medium chain fatty acid (C6-C12) | 2-8% |
| Lysine or arginine | 1-2% |
| SEQ ID NO 12 (P228) | 10-1,000 ppm* |

*From Therapeutic Peptides Inc. (Baton Rouge, LA)

Mix Phase B into Phase A with a high speed homogenizer at 10,000—1200 rpm at 30-40° C. for about 10 minutes. The resulting mixture is then processed in a colloid mill at greater than about 10,000 psi to produce particles sizes of less than about 200 nm. The resulting concentrate is added to a conventional macroemulsion cream at a concentration of from about 1 to about 20%.

Example 2

Anti-Aging Facial Gel

| | | |
|---|---|---|
| 1. | DI Water | 95-98% |
| 2. | Xanthan gum | 0.1-0.3% |
| 3. | Magnesium ascorbyl phosphate | 1-3% |
| 4. | SEQ ID NO 14 (P266)* | 10-1,000 ppm |
| 5. | Sodium Hydroxymethylglycinate** | 0.3-1% |

*From Therapeutic Peptides Inc. (Baton Rouge, LA)
**Suttocide A from Sutton Labs (Chatham, NJ)

Add Ingredients 2-5 to DI Water (#1) while mixing at 1,000 rpm in a Silverson mixer until homogenous.

Example 3

Night Eye Cream

| Part A | |
|---|---|
| Ascorbyl Palmitate | 1.00 |
| BHT | 0.20 |
| SD Alcohol 40-B | 1.50 |
| Part B | |
| Sesamum Indicum (Sesame) Seed Oil | 1.00 |
| Ceramide 3 | 0.50 |
| Part C | |
| Glycerin | 1.50 |
| PEG-60 Almond Glycerides | 1.00 |
| Isopropylparaben, Isobutylparaben, Butylparaben | 1.00 |
| Part D | |
| Retinyl Palmitate | 1.00 |
| Tocopheryl Acetate | 1.00 |
| $C_{30-45}$ Alkyl Methicone | 1.00 |
| $C_{12-15}$ Alkyl Benzoate | 7.50 |
| Dimethicone | 2.00 |

-continued

| Part E | |
|---|---|
| Magnesium Ascorbyl Phosphate | 3.00 |
| Ethylhexyl Palmitate, Tribehenin, Sorbitan Isostearate, SEQ ID NO 22 (P382) | 3.00 |
| Part F | |
| SD Alcohol 40-B, SEQ ID NO 23 (P387) | 0.50 |
| PEG-60 Almond Glycerides, SEQ ID NO 25 (P394) | 0.04 |
| Cyclomethicone, Dimethicone Crosspolymer | 71.81 |
| Soybean Oil, Retinol | 1.00 |
| Fragrance | 0.45 |

Add Phase A ingredients to the main vessel; mix at 400 rpm while heating to 45-55° C. Sequentially add Parts B then C then D to main vessel while mixing at 400-800 rpm. Homogenize with Silverson mixer at 2500 rpm while adding Part E. Add Part F and homogenize at 2500 rpm while mixing at 1000-1700 rpm.

Example 4

SPF 25 Sunscreen

| Part A | |
|---|---|
| Cylcopentasiloxane, Titanium Dioxide, Alumina, PEG-10 Dimethicone, Methicone | 60.00 |
| Zinc Oxide, Cyclopentasiloxane, PEG-10 Dimethicone, Methicone | 8.00 |
| Cyclomethicone, Dimethiconol | 1.00 |
| Sorbitan Isostearate | 1.50 |
| Part B | |
| Dimethicone/Vinyl Dimethicone Crosspolymer | 4.00 |
| Iron Oxide (Black) | 0.02 |
| Iron Oxide (Red) | 0.09 |
| Iron Oxide (Yellow) | 0.25 |
| Part C | |
| Cyclomethicone, DimethiconeCrosspolymer | 21.90 |
| Part D | |
| Tribehenin, Calcium Behenate | 2.25 |
| Part E | |
| Lecithin, SD Alcohol 40-B | 0.50 |
| Caprylic/Capric Triglyceride, Ceramidelll A, Cholesterol, Tocopheryl Acetate, Squalene, Retinyl Palmitate, SEQ ID NO 1 (P291) | 10.50 |

Add Part A to main vessel. Heat to 110° C. with mixing at 300-600 rpm. Homogenize Part B ingredients together with Silverson mixer. Add Part B to Part A. Add Parts C and D to Parts A and B. Homogenize with Silverson mixer at 1500-2500 rpm. Cool to 70° C. with mixing. Add Part E to above mixture; continue mixing until homogenous.

Example 5

Anti-Aging Cream

| Part A | |
|---|---|
| Water | 70.27 |
| 1,3-β-D-Glucan lactate (non-yeast derived) | 0.04 |
| Magnesium Ascorbyl Phosphate | 0.40 |

-continued

| Part B | |
|---|---|
| Behenoxy Dimethicone | 1.60 |
| Cyclomethicone | 5.10 |
| Tocopheryl Acetate | 0.20 |
| Behentrimonium Methosulfate, Cetearyl Alcohol | 3.60 |
| Dimethicone | 2.10 |
| Behenyl Alcohol | 1.60 |
| Glycerin, Lecithin, Palmitoyl Myristyl Serinate | 0.50 |
| Palmitoyl Hydrolyzed Wheat Protein | 0.30 |
| Cetearyl Alcohol, Cetearyl Glucoside | 2.00 |
| Part C | |
| PEG-7 Glyceryl Cocoate, PPG-2-Cetearteth-9, Centaury (*Centaurium Erythraea*) Extract | 4.00 |
| Glycerin, Water, *Siegesbeckia Orientelis* Extract | 4.00 |
| Glyceryl Polymethacrylate, PEG-8, SEQ ID NO 60 (P373) | 2.00 |
| PEG-60 Almond Glycerides, SEQ ID NO 27 (P401) | 1.00 |
| Part D | |
| Pheonxyethanol, Methylparaben, Butylparaben, Ethylparaben, Propylparaben, Isobutylparaben | 0.70 |
| Fragrance | 0.50 |

Add Part A ingredients to main vessel. Mix at 500 rpm while heating to 70° C. Mix and heat Part B ingredients to 75° C. at 500 rpm. Add Part B to Part A while mixing at 500-1500 rpm. Cool to 55° C. while mixing at 1200-1600 rpm. Add Part C while mixing at 1200-1600 rpm. Cool to 45° C. while mixing at 1200-1600 rpm. Add Part D to A-B-C and homogenize for 5 min per 10 kg at 3000 rpm with the Silverson overhead homogenizer.

Example 6

Conditioning Hair Mask

| Phase A | |
|---|---|
| Quaternium-91 (and) Cetrimonium Methosulfate (and) Cetearyl Alcohol [1] | 1.50 |
| Behentrimonium Methosulfate (and) Cetyl Alcohol (and) Butylene Glycol [2] | 0.80 |
| Quaternium-93 (and) Dipropylene Glycol [3] | 0.50 |
| Stearamidopropyl Dimethylamine | 0.30 |
| Cetyl Ester | 1.50 |
| Stearyl Alcohol | 3.00 |
| PPG-3 Benzyl Ether Myristate | 4.00 |
| *Olea Europea* (Olive) Fruit Oil | 1.00 |
| *Prunus Amygdalus Dulcis* (Sweet Almond) Oil | 1.00 |
| *Limnanthes Alba* (Meadowfoam) Seed Oil | 1.00 |
| Phase B | |
| Deionized Water | q.s. to 100 |
| Citric Acid Crystals | 0.05 |
| Phase C | |
| Glycerin (and) Water (and) *Camellia Sinensis* Extract [4] | 0.05 |
| Propylene Glycol (and) Water and *Rheum Palmatum* Extract [5] | 0.05 |
| Butylene Glycol (and) Water (and) *Chamomilla Recutita* [6] | 0.05 |
| Phenoxyethanol (and) Methylparaben (and) Ethylparaben (and) Propylparaben (and) Butylparaben (and) Isobutylparaben [7] | 0.05 |
| SEQ ID NO 75 (P226) | 10-1,000 ppm |
| SEQ ID NO 69 (P288) | 10-1,000 ppm |
| Phase D | |
| Hydrolyzed Vegetable Protein PG-Propyl Silanetriol | 1.00 |

[1, 2, 3, 4] Commercially-available from Croda Inc. (Edison, NJ) under the respective tradenames Crodazosoft DBQ, Incroquat Behenyl TMS-50, Incroquat 18-MEA-40 and Crodarom Green Tea.
[5, 6] Commercially-available from Active Organics LP (Lewisville, TX) under the tradenames Actiphyte of Rhubarb PG50 and Actiphyte of Chamomile BG50.
[7] Commercially-available as Phenonip from Clariant Corp. (Mount Holly, NC)

Combine ingredients of phase A and B separately with mixing and heat to 75-80° C. Add phase B to phase A, mixing well. Cool to 50° C. and add ingredients to phase C with mixing. Cool to 35° C. and add phase D. Cool to room temperature and adjust pH to 4.5, if necessary.

Example 7

Conditioning Mascara

| Phase A | |
|---|---|
| Hydrogenated polycyclopentadiene (and) isododecane | 14.29 |
| Isododecane | 24.64 |
| Phase B | |
| Lithium magnesium silicate | 2.00 |
| SD alcohol | 1.00 |
| Phase C | |
| Iron oxide [C.I. 77499] | 7.00 |
| Polymethylsylsesquioxane | 2.00 |
| Silica | 1.00 |
| Mica (and) titanium dioxide | 1.00 |
| Cyclomethicone (and) PEG/PPG-20/15 dimethicone | 3.00 |
| Isododecane | 10.00 |
| Phase D | |
| Sodium chloride | 0.25 |
| Deionized water | 11.50 |
| Methylparaben | 0.10 |
| Phase E | |
| $C_{18-36}$ triglycerides | 5.00 |
| Beeswax SP422 | 6.00 |
| Carnauba wax | 3.00 |
| Polyethylene 617A | 3.00 |
| Propylparaben | 0.10 |
| Phase F | |
| Deionized water | 2.00 |
| Panthenol | 0.35 |
| Imidazolidinyl urea | 0.25 |
| SEQ ID NO 85 (P222) | 10-1,000 ppm |
| SEQ ID NO 80 (P214) | 10-1,000 ppm |
| Phase G | |
| Isododecane | 2.00 |
| Cellulose | 0.50 |

Combine Phase A materials. Slowly add lithium magnesium silicate. Stir at high speed for 20 minutes. Add SD alcohol and stir an additional 20 minutes. Combine Phase C ingredients and stir at a high speed for 45 minutes. Add gel phase (A-B) to Phase C to form a base. Combine phase D ingredients and stir until clear. Add Phase D slowly to the base (Phases A-B-C); continue homogenizing while heating to 85° C. Add the waxes (Phase E) at 70° C. to the base (Phases A-B-C-D); continue to homogenize. Begin air cooling. At 65° C., QS solvent loss. At 42° C., add the Phase F solution. At 38° C., add the Phase G slurry. Continue homogenizing and cool to 25° C.

Example 8

Improvement in Signs of Aging

The efficacy of topical compositions comprising therapeutically effective amounts of oligomeric acylated biosurfactants of the present invention in reducing the signs of aging is measurable by reduction in the severity of superficial lines in the "Crow's Feet" area, by clinical assessment of skin texture and tone, and by self-assessment. In addition to these improvements in appearance, improvements in biophysical parameters, including skin tautness and elasticity, are measurable with a Twistometer.

Twenty adult female Caucasian subjects, ranging in age from mid-thirties to late-sixties, are enrolled in a Study. They are selected for mild to moderate photodamage, as specified in the Protocol. The subjects are clinically assessed at each Study visit, by the Principal Investigator, or by the Research Associate. Superficial facial lines (SFL) in the "Crow's Feet" (periorbital) area are assessed by the method of Packman and Gans. Packman, E. W., and Gans, E. H, "Topical moisturizers: quantification of their effect on superficial facial lines" J. Soc. Cosmet. Chem. 9: 1-11 (1978). The SFL score is a weighted sum of the numbers of lines/wrinkles of three classes, of increasing severity; shallow (n×I), definite (n×2), and deep (n×3). Severity of the flaws grouped in Skin Surface Texture and Tone (Table 3) are scored with a 0-10 analog scale.

Color photographs are taken with a Nikon D70 digital camera, under standardized conditions, with the camera mounted on a focusing stage, to assure that the reproduction ratio (magnification) is the same each time. Black and white photos are taken similarly, with a Nikon F-100 film camera, using T-max 100 print film, and using a UVA filter on the camera lens.

At the end of an eight-week study, expert graders assess overall improvement in appearance from Baseline, using the color photographs. Assessment is made of changes in individual skin characteristics, including the extent to which the skin appears smoother and less lined, pores are less evident, and skin color becomes more uniform.

Skin tautness and elasticity are measured with a Twistometer, of the type described by Finlay. Finlay, J. B. "The torsional characteristics of human skin in vivo." Biomed. Eng. 6: 567-573 (1971). Torsional stretch and rebound are measured, with a disc attached to the skin surface with adhesive tape, and rotated by a small electrical current which is held constant for a fixed period of time. The angle through which the attached disc can rotate is inversely related to skin tautness, and the elasticity of the twisted skin is directly related to the extent of the rebound when the current is turned off. Thus, a decrease in the torsional stretch indicates the skin has become more taut (firm), and an increase in the rebound that it has become more elastic.

Except for Twistometer measurements, non-parametric tests are used (Wilcoxon's Signed Ranks Test, or the 50% Probability Test) for assessing the statistical significance of changes in skin condition. These tests require no assumption of normal distribution, and are appropriate for analysis of scoring done with an ordinal or nominal scale, or for "yes or no" answers. For instrumental measurements, a paired difference "t-test" analysis for comparing "before" and "after" scores on the same subjects is used.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

The invention claimed is:

1. An oligomeric acylated biosurfactant having from five to nine amino acids, of which three or four amino acids are lysine, and among the three or four lysine amino acids there is at least one dilysinyl dipeptide, wherein the oligomeric acylated biosurfactant conforms to the structure Acyl-$Q1_w$-$Q2_x$-Lys-Q3-Lys-$Q4_y$-$Q5_z$-Term wherein Acyl is selected from the group of myristoyl and palmitoyl Term is selected from the group of acid and amide w is an integer from zero to two, with the proviso that when w is one Q1 is selected from Leu, Ala and Pro, and with the further proviso that when w is two Q1 is Leu Ala x is an integer from zero to one, with the proviso that when x is one Q2 is Lys Q3 is a dipeptide selected from Ala Leu and Leu Ala y is an integer from zero to one, with the proviso that when y is one Q4 is Lys z is an integer from zero to two, with the proviso that when z is one Q5 is selected from Leu and Ala, and with the further proviso that when z is two Q5 is Ala Phe wherein the sum of x and y is either one or two and the oligomeric acylated biosurfactant has a critical micelle concentration of less than about 200 ppm in an aqueous environment of MEM Solution that reduces the surface tension of the MEM Solution to less than about 50 dynes/cm$^2$.

2. The oligomeric acylated biosurfactant of claim 1 wherein the oligomeric acylated biosurfactant is selected from SEQ ID NO 16; SEQ ID NO 17; SEQ ID NO 18; SEQ ID NO 28; SEQ ID NO 30; SEQ ID NO 31; SEQ ID NO 32; SEQ ID NO 33; SEQ ID NO 34; SEQ ID NO 35; SEQ ID NO 44; SEQ ID NO 45; SEQ ID NO 49; SEQ ID NO 50; SEQ ID NO 51; SEQ ID NO 55; SEQ ID NO 56; SEQ ID NO 62; SEQ ID NO 63; SEQ ID NO 64; SEQ ID NO 75; SEQ ID NO 76; SEQ ID NO 80; SEQ ID NO 81; SEQ ID NO 82; SEQ ID NO 83; SEQ ID NO 86; SEQ ID NO 87; SEQ ID NO 88; SEQ ID NO 91; SEQ ID NO 92; SEQ ID NO 93; SEQ ID NO 98; and SEQ ID NO 99.

3. A topically-applied dermatocosmetic composition comprising (i) an oligomeric acylated biosurfactant according to claim 2 and (ii) at least one active ingredient selected from the group of peptides and peptide derivatives, retinoids, antioxidants and radical scavengers, vitamins, minerals, sugar amines, anti-inflammatory agents, phytosterols and/or plant hormones, protease inhibitors, penetration enhancers, skin soothing and/or healing agents, anti-acne agents, antimicrobial agents, skin bleaching and lightening agents, external analgesics, sunscreen actives, humectants, moisturizers, and skin-conditioning agents and (iii) a dermatocosmetic carrier comprising one or more ingredients selected from the group consisting of: natural oils; silicone fluids, elastomers and resins; hydrocarbon fluids; surfactants and emulsifiers; abrasives and exfoliants; absorbents and astringents; preservatives; film formers and other polymeric materials that increase the substantivity of topical compositions to the skin; thickening agents and fillers; and pH adjusters.

4. The topically-applied dermatocosmetic composition according to claim 3 wherein the at least one active ingredient is a retinoid selected from the group consisting of retinol, retinol palmitate, and retinoic acid.

5. A hair care preparation comprising at least one oligomeric acylated biosurfactant according to claim 1 wherein the one oligomeric acylated biosurfactant is selected from the group consisting of SEQ ID NO 75; SEQ ID NO 80; SEQ ID NO 83; SEQ ID NO 86; and SEQ ID NO 99.

* * * * *

SEQUENCE LISTING

<160> NUMBER OF SEQ ID NOS: 100

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (4)..(4)
<223> OTHER INFORMATION: amide-terminated amino acid

<400> SEQUENCE: 1

Lys Lys Ala Leu
1

<210> SEQ ID NO 2
<211> LENGTH: 4
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated

<400> SEQUENCE: 2

Lys Lys Ala Leu
1

<210> SEQ ID NO 3
<211> LENGTH: 4
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated

<400> SEQUENCE: 3

Leu Ala Lys Lys
1

<210> SEQ ID NO 4
<211> LENGTH: 4
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated

<400> SEQUENCE: 4

Ile Ala Lys Lys
1

<210> SEQ ID NO 5
<211> LENGTH: 4
<212> TYPE: PRT

```
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (4)..(4)
<223> OTHER INFORMATION: amide-terminated amino acid

<400> SEQUENCE: 5

Leu Ser Lys Lys
1

<210> SEQ ID NO 6
<211> LENGTH: 4
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)

<400> SEQUENCE: 6

Asp Asp Ala Asp
1

<210> SEQ ID NO 7
<211> LENGTH: 4
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Palmitoylated
<220> FEATURE:
<221> NAME/KEY: MISC_FEATURE
<222> LOCATION: (4)..(4)
<223> OTHER INFORMATION: amide-terminated amino acid

<400> SEQUENCE: 7

Ala Ala Lys Arg
1

<210> SEQ ID NO 8
<211> LENGTH: 4
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (4)..(4)
<223> OTHER INFORMATION: amide-terminated amino acid

<400> SEQUENCE: 8

Gly Gly Lys Arg
1

<210> SEQ ID NO 9
<211> LENGTH: 4
<212> TYPE: PRT
<213> ORGANISM: Artificial Sequence
```

```
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (4)..(4)
<223> OTHER INFORMATION: amide-terminated amino acid

<400> SEQUENCE: 9

Ala Ala Lys Arg
1

<210> SEQ ID NO 10
<211> LENGTH: 4
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (4)..(4)
<223> OTHER INFORMATION: amide-terminated amino acid
<220> FEATURE:
<221> NAME/KEY: MISC_FEATURE
<222> LOCATION: (4)..(4)
<223> OTHER INFORMATION: The amino acid at this location is a
      "d" amino acid.

<400> SEQUENCE: 10

Lys Gly Leu Lys
1

<210> SEQ ID NO 11
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (5)..(5)
<223> OTHER INFORMATION: amide-terminated amino acid

<400> SEQUENCE: 11

Lys Thr Thr Lys Ser
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (5)..(5)
<223> OTHER INFORMATION: amide-terminated amino acid

<400> SEQUENCE: 12
```

```
Thr Lys Thr Thr Lys
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Palmitoylated

<400> SEQUENCE: 13

Lys Lys Gly Glu Met
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated

<400> SEQUENCE: 14

Gly Arg Lys Gly Asp
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated

<400> SEQUENCE: 15

Lys Lys Gly Glu Met
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Dodecyl
<220> FEATURE:
<221> NAME/KEY: MISC_FEATURE
<222> LOCATION: (5)..(5)
<223> OTHER INFORMATION: amide-terminated amino acid

<400> SEQUENCE: 16

Lys Lys Ala Leu Lys
1               5

<210> SEQ ID NO 17
<211> LENGTH: 5
<212> TYPE: PRT
```

```
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated

<400> SEQUENCE: 17

Lys Lys Ala Leu Lys
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated

<400> SEQUENCE: 18

Lys Leu Ala Lys Lys
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (2)..(2)
<223> OTHER INFORMATION: The amino acid at this location is a "d"
     amino acid.
<220> FEATURE:
<221> NAME/KEY: MISC_FEATURE
<222> LOCATION: (4)..(4)
<223> OTHER INFORMATION: The amino acid at this location is a "d"
     amino acid.
<220> FEATURE:
<221> NAME/KEY: MISC_FEATURE
<222> LOCATION: (5)..(5)
<223> OTHER INFORMATION: amide-terminated amino acid

<400> SEQUENCE: 19

Lys Lys Ala Leu Lys
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (5)..(5)
<223> OTHER INFORMATION: amide-terminated amino acid
<220> FEATURE:
<221> NAME/KEY: MISC_FEATURE
<222> LOCATION: (5)..(5)
<223> OTHER INFORMATION: The amino acid at this location is a "d"
``` amino acid.

<400> SEQUENCE: 20

Lys Lys Leu Ala Lys
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (5)..(5)
<223> OTHER INFORMATION: amide-terminated amino acid

<400> SEQUENCE: 21

Lys Lys Gly Leu Lys
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (5)..(5)
<223> OTHER INFORMATION: amide-terminated amino acid

<400> SEQUENCE: 22

Gly Arg Gly Asp Ser
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Octoylated
<220> FEATURE:
<221> NAME/KEY: MISC_FEATURE
<222> LOCATION: (5)..(5)
<223> OTHER INFORMATION: amide-terminated amino acid

<400> SEQUENCE: 23

Gly Arg Gly Asp Ser
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)

-continued

```
<223> OTHER INFORMATION: Myristoylated
<220> FEATURE:
<221> NAME/KEY: MISC_FEATURE
<222> LOCATION: (5)..(5)
<223> OTHER INFORMATION: amide-terminated amino acid
<220> FEATURE:
<221> NAME/KEY: MISC_FEATURE
<222> LOCATION: (5)..(5)
<223> OTHER INFORMATION: The amino acid at this location is a "d"
      amino acid.

<400> SEQUENCE: 24

Lys Lys Gly Ile Lys
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (5)..(5)
<223> OTHER INFORMATION: amide-terminated amino acid
<220> FEATURE:
<221> NAME/KEY: MISC_FEATURE
<222> LOCATION: (5)..(5)
<223> OTHER INFORMATION: The amino acid at this location is a "d"
      amino acid.

<400> SEQUENCE: 25

Lys Lys Gly Leu Lys
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (5)..(5)
<223> OTHER INFORMATION: amide-terminated amino acid
<220> FEATURE:
<221> NAME/KEY: MISC_FEATURE
<222> LOCATION: (5)..(5)
<223> OTHER INFORMATION: The amino acid at this location is a "d"
      amino acid.

<400> SEQUENCE: 26

Lys Lys Ser Leu Lys
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
```

```
<221> NAME/KEY: MISC_FEATURE
<222> LOCATION: (5)..(5)
<223> OTHER INFORMATION: amide-terminated amino acid
<220> FEATURE:
<221> NAME/KEY: MISC_FEATURE
<222> LOCATION: (5)..(5)
<223> OTHER INFORMATION: The amino acid at this location is a "d"
      amino acid.

<400> SEQUENCE: 27

Lys Ile Ala Lys Lys
1               5

<210> SEQ ID NO 28
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (5)..(5)
<223> OTHER INFORMATION: amide-terminated amino acid
<220> FEATURE:
<221> NAME/KEY: MISC_FEATURE
<222> LOCATION: (5)..(5)
<223> OTHER INFORMATION: The amino acid at this location is a "d"
      amino acid.

<400> SEQUENCE: 28

Lys Leu Ala Lys Lys
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (5)..(5)
<223> OTHER INFORMATION: Myristoylated
<220> FEATURE:
<221> NAME/KEY: MISC_FEATURE
<222> LOCATION: (5)..(5)
<223> OTHER INFORMATION: amide-terminated amino acid

<400> SEQUENCE: 29

Ile Ile Ile Lys Lys
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated

<400> SEQUENCE: 30

Lys Leu Ala Lys Lys Ala
1               5

<210> SEQ ID NO 31
```

```
<211> LENGTH: 6
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated

<400> SEQUENCE: 31

Ala Lys Lys Leu Ala Lys
1               5

<210> SEQ ID NO 32
<211> LENGTH: 6
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (1)..(6)
<223> OTHER INFORMATION: The amino acids at these locations are "d"
      amino acids.

<400> SEQUENCE: 32

Leu Lys Lys Ala Leu Lys
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (6)..(6)
<223> OTHER INFORMATION: amide-terminated amino acid

<400> SEQUENCE: 33

Leu Lys Lys Ala Leu Lys
1               5

<210> SEQ ID NO 34
<211> LENGTH: 6
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (6)..(6)
<223> OTHER INFORMATION: amide-terminated amino acid

<400> SEQUENCE: 34

Pro Lys Lys Ala Leu Lys
1               5
```

```
<210> SEQ ID NO 35
<211> LENGTH: 6
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (6)..(6)
<223> OTHER INFORMATION: amide-terminated amino acid
<220> FEATURE:
<221> NAME/KEY: MISC_FEATURE
<222> LOCATION: (6)..(6)
<223> OTHER INFORMATION: The amino acid at this location is a "d"
     amino acid.

<400> SEQUENCE: 35

Lys Leu Ala Lys Lys Leu
1               5

<210> SEQ ID NO 36
<211> LENGTH: 6
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (1)..(6)
<223> OTHER INFORMATION: The amino acid at this location is a "d"
     amino acid.
<220> FEATURE:
<221> NAME/KEY: MISC_FEATURE
<222> LOCATION: (6)..(6)
<223> OTHER INFORMATION: amide-terminated amino acid

<400> SEQUENCE: 36

Ala Lys Lys Gly Leu Lys
1               5

<210> SEQ ID NO 37
<211> LENGTH: 6
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (1)..(6)
<223> OTHER INFORMATION: The amino acid at this location is a "d"
     amino acid.
<220> FEATURE:
<221> NAME/KEY: MISC_FEATURE
<222> LOCATION: (6)..(6)
<223> OTHER INFORMATION: amide-terminated amino acid

<400> SEQUENCE: 37

Gly Lys Lys Ala Leu Lys
1               5

<210> SEQ ID NO 38
<211> LENGTH: 6
```

```
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (6)..(6)
<223> OTHER INFORMATION: The amino acid at this location is a "d"
     amino acid.

<400> SEQUENCE: 38

Leu Lys Lys Ala Leu Lys
1               5

<210> SEQ ID NO 39
<211> LENGTH: 6
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (6)..(6)
<223> OTHER INFORMATION: amide-terminated amino acid
<220> FEATURE:
<221> NAME/KEY: MISC_FEATURE
<222> LOCATION: (6)..(6)
<223> OTHER INFORMATION: The amino acid at this location is a "d"
     amino acid.

<400> SEQUENCE: 39

Ser Lys Lys Ala Leu Lys
1               5

<210> SEQ ID NO 40
<211> LENGTH: 6
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (6)..(6)
<223> OTHER INFORMATION: amide-terminated amino acid

<400> SEQUENCE: 40

Asp Asp Ser Ser Lys Lys
1               5

<210> SEQ ID NO 41
<211> LENGTH: 6
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (6)..(6)
```

<223> OTHER INFORMATION: amide-terminated amino acid

<400> SEQUENCE: 41

Asp Asp Leu Ala Lys Lys
1               5

<210> SEQ ID NO 42
<211> LENGTH: 6
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (6)..(6)
<223> OTHER INFORMATION: amide-terminated amino acid

<400> SEQUENCE: 42

Ile Ile Ile Ile Ile Lys
1               5

<210> SEQ ID NO 43
<211> LENGTH: 4
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated

<400> SEQUENCE: 43

Asp Ser Asp Asp
1

<210> SEQ ID NO 44
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (1)..(5)
<223> OTHER INFORMATION: The amino acids at these positions are "d"
      amino acids.
<220> FEATURE:
<221> NAME/KEY: MISC_FEATURE
<222> LOCATION: (5)..(5)
<223> OTHER INFORMATION: amide-terminated amino acid

<400> SEQUENCE: 44

Lys Lys Ala Leu Lys
1               5

<210> SEQ ID NO 45
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE

```
<222> LOCATION: (1)..(1)
<223> OTHER INFORMATION: Myristoylated
<220> FEATURE:
<221> NAME/KEY: MISC_FEATURE
<222> LOCATION: (1)..(1)
<223> OTHER INFORMATION: The amino acid at this location is a "d"
      amino acid.
<220> FEATURE:
<221> NAME/KEY: MISC_FEATURE
<222> LOCATION: (5)..(5)
<223> OTHER INFORMATION: amide-terminated amino acid

<400> SEQUENCE: 45

Lys Lys Ala Leu Lys
1               5

<210> SEQ ID NO 46
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (5)..(5)
<223> OTHER INFORMATION: amide-terminated amino acid

<400> SEQUENCE: 46

Lys Lys Gly Ile Lys
1               5

<210> SEQ ID NO 47
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (5)..(5)
<223> OTHER INFORMATION: amide-terminated amino acid

<400> SEQUENCE: 47

Lys Ile Ala Lys Lys
1               5

<210> SEQ ID NO 48
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated

<400> SEQUENCE: 48

Ala Gly Glu Arg Ala
1               5

<210> SEQ ID NO 49
<211> LENGTH: 6
<212> TYPE: PRT
```

```
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (6)..(6)
<223> OTHER INFORMATION: amide-terminated amino acid

<400> SEQUENCE: 49

Lys Leu Ala Lys Lys Leu
1               5

<210> SEQ ID NO 50
<211> LENGTH: 6
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (6)..(6)
<223> OTHER INFORMATION: amide-terminated amino acid

<400> SEQUENCE: 50

Leu Lys Leu Ala Lys Lys
1               5

<210> SEQ ID NO 51
<211> LENGTH: 6
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (6)..(6)
<223> OTHER INFORMATION: amide-terminated amino acid
<220> FEATURE:
<221> NAME/KEY: MISC_FEATURE
<222> LOCATION: (6)..(6)
<223> OTHER INFORMATION: The amino acid at this location is a "d"
      amino acid.

<400> SEQUENCE: 51

Leu Lys Leu Ala Lys Lys
1               5

<210> SEQ ID NO 52
<211> LENGTH: 6
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (1)..(6)
<223> OTHER INFORMATION: The amino acid at this location is a "d"
      amino acid.
```

```
<220> FEATURE:
<221> NAME/KEY: MISC_FEATURE
<222> LOCATION: (6)..(6)
<223> OTHER INFORMATION: amide-terminated amino acid

<400> SEQUENCE: 52

Ala Lys Lys Ala Leu Lys
1               5

<210> SEQ ID NO 53
<211> LENGTH: 6
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (6)..(6)
<223> OTHER INFORMATION: amide-terminated amino acid

<400> SEQUENCE: 53

Lys Lys Lys Ile Ile Ile
1               5

<210> SEQ ID NO 54
<211> LENGTH: 4
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Palmitoylated
<220> FEATURE:
<221> NAME/KEY: MISC_FEATURE
<222> LOCATION: (4)..(4)
<223> OTHER INFORMATION: amide-terminated amino acid

<400> SEQUENCE: 54

Ala Ala Arg Lys
1

<210> SEQ ID NO 55
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Palmitoylated
<220> FEATURE:
<221> NAME/KEY: MISC_FEATURE
<222> LOCATION: (5)..(5)
<223> OTHER INFORMATION: amide-terminated amino acid

<400> SEQUENCE: 55

Lys Lys Leu Ala Lys
1               5

<210> SEQ ID NO 56
<211> LENGTH: 6
<212> TYPE: PRT
<213> ORGANISM: Artificial Sequence
<220> FEATURE:
<223> OTHER INFORMATION: Synthetic peptide sequence
```

```
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (6)..(6)
<223> OTHER INFORMATION: amide-terminated amino acid

<400> SEQUENCE: 56

Lys Lys Ala Leu Lys Leu
1               5

<210> SEQ ID NO 57
<211> LENGTH: 4
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Palmitoylated
<220> FEATURE:
<221> NAME/KEY: MISC_FEATURE
<222> LOCATION: (4)..(4)
<223> OTHER INFORMATION: amide-terminated amino acid

<400> SEQUENCE: 57

Lys Ala Lys Leu
1

<210> SEQ ID NO 58
<211> LENGTH: 4
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Palmitoylated
<220> FEATURE:
<221> NAME/KEY: MISC_FEATURE
<222> LOCATION: (4)..(4)
<223> OTHER INFORMATION: amide-terminated amino acid

<400> SEQUENCE: 58

Leu Ala Lys Lys
1

<210> SEQ ID NO 59
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (1)..(1)
<223> OTHER INFORMATION: The amino acid at this location is a "d"
      amino acid.
<220> FEATURE:
<221> NAME/KEY: MISC_FEATURE
<222> LOCATION: (3)..(3)
<223> OTHER INFORMATION: The amino acid at this location is a "d"
      amino acid.
<220> FEATURE:
<221> NAME/KEY: MISC_FEATURE
<222> LOCATION: (5)..(5)
```

```
<223> OTHER INFORMATION: amide-terminated amino acid
<220> FEATURE:
<221> NAME/KEY: MISC_FEATURE
<222> LOCATION: (5)..(5)
<223> OTHER INFORMATION: The amino acid at this location is a "d"
      amino acid.

<400> SEQUENCE: 59

Lys Lys Ala Leu Lys
1               5

<210> SEQ ID NO 60
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (5)..(5)
<223> OTHER INFORMATION: amide-terminated amino acid

<400> SEQUENCE: 60

Lys Lys Ser Leu Lys
1               5

<210> SEQ ID NO 61
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (5)..(5)
<223> OTHER INFORMATION: amide-terminated amino acid

<400> SEQUENCE: 61

Leu Ala Ile Lys Lys
1               5

<210> SEQ ID NO 62
<211> LENGTH: 6
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (6)..(6)
<223> OTHER INFORMATION: amide-terminated amino acid

<400> SEQUENCE: 62

Lys Lys Ala Leu Lys Lys
1               5

<210> SEQ ID NO 63
<211> LENGTH: 6
<212> TYPE: PRT
<213> ORGANISM: Artificial Sequence
```

```
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (6)..(6)
<223> OTHER INFORMATION: amide-terminated amino acid

<400> SEQUENCE: 63

Lys Lys Ala Leu Lys Ala
1               5

<210> SEQ ID NO 64
<211> LENGTH: 6
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (6)..(6)
<223> OTHER INFORMATION: amide-terminated amino acid

<400> SEQUENCE: 64

Leu Lys Lys Ala Leu Lys
1               5

<210> SEQ ID NO 65
<211> LENGTH: 6
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (6)..(6)
<223> OTHER INFORMATION: amide-terminated amino acid

<400> SEQUENCE: 65

Ile Ile Ile Lys Lys Lys
1               5

<210> SEQ ID NO 66
<211> LENGTH: 4
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (4)..(4)
<223> OTHER INFORMATION: amide-terminated amino acid

<400> SEQUENCE: 66

Ser Asp Gly Arg
1
```

```
<210> SEQ ID NO 67
<211> LENGTH: 4
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (4)..(4)
<223> OTHER INFORMATION: amide-terminated amino acid

<400> SEQUENCE: 67

Leu Lys Ala Lys
1

<210> SEQ ID NO 68
<211> LENGTH: 6
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Palmitoylated
<220> FEATURE:
<221> NAME/KEY: MISC_FEATURE
<222> LOCATION: (6)..(6)
<223> OTHER INFORMATION: amide-terminated amino acid

<400> SEQUENCE: 68

Val Gly Val Ala Pro Gly
1               5

<210> SEQ ID NO 69
<211> LENGTH: 4
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (4)..(4)
<223> OTHER INFORMATION: amide-terminated amino acid

<400> SEQUENCE: 69

Lys Ala Lys Ala
1

<210> SEQ ID NO 70
<211> LENGTH: 4
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (4)..(4)
<223> OTHER INFORMATION: amide-terminated amino acid

<400> SEQUENCE: 70
```

Ala Lys Ala Lys
1

<210> SEQ ID NO 71
<211> LENGTH: 4
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Palmitoylated
<220> FEATURE:
<221> NAME/KEY: MISC_FEATURE
<222> LOCATION: (4)..(4)
<223> OTHER INFORMATION: amide-terminated amino acid

<400> SEQUENCE: 71

Gly Arg Lys Gly
1

<210> SEQ ID NO 72
<211> LENGTH: 4
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (4)..(4)
<223> OTHER INFORMATION: amide-terminated amino acid

<400> SEQUENCE: 72

Gly Arg Lys Gly
1

<210> SEQ ID NO 73
<211> LENGTH: 4
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (4)..(4)
<223> OTHER INFORMATION: amide-terminated amino acid

<400> SEQUENCE: 73

Leu Ala Lys Lys
1

<210> SEQ ID NO 74
<211> LENGTH: 4
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Palmitoylated
<220> FEATURE:
<221> NAME/KEY: MISC_FEATURE
<222> LOCATION: (4)..(4)

```
<223> OTHER INFORMATION: amide-terminated amino acid

<400> SEQUENCE: 74

Gly Gln Pro Arg
1

<210> SEQ ID NO 75
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (5)..(5)
<223> OTHER INFORMATION: amide-terminated amino acid

<400> SEQUENCE: 75

Lys Leu Ala Lys Lys
1               5

<210> SEQ ID NO 76
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Palmitoylated

<400> SEQUENCE: 76

Lys Leu Ala Lys Lys
1               5

<210> SEQ ID NO 77
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (5)..(5)
<223> OTHER INFORMATION: amide-terminated amino acid

<400> SEQUENCE: 77

Lys Lys Gly Glu Met
1               5

<210> SEQ ID NO 78
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (5)..(5)
```

```
<223> OTHER INFORMATION: amide-terminated amino acid

<400> SEQUENCE: 78

Lys Arg Gly Lys Pro
1               5

<210> SEQ ID NO 79
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Palmitoylated

<400> SEQUENCE: 79

Lys Arg Gly Asp Arg
1               5

<210> SEQ ID NO 80
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (5)..(5)
<223> OTHER INFORMATION: amide-terminated amino acid

<400> SEQUENCE: 80

Lys Lys Ala Leu Lys
1               5

<210> SEQ ID NO 81
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Palmitoylated
<220> FEATURE:
<221> NAME/KEY: MISC_FEATURE
<222> LOCATION: (5)..(5)
<223> OTHER INFORMATION: amide-terminated amino acid

<400> SEQUENCE: 81

Lys Lys Ala Leu Lys
1               5

<210> SEQ ID NO 82
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Palmitoylated

<400> SEQUENCE: 82
```

```
Lys Lys Ala Leu Lys
1               5

<210> SEQ ID NO 83
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (5)..(5)
<223> OTHER INFORMATION: amide-terminated amino acid

<400> SEQUENCE: 83

Lys Lys Leu Ala Lys
1               5

<210> SEQ ID NO 84
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Palmitoylated

<400> SEQUENCE: 84

Gly Arg Lys Gly Asp
1               5

<210> SEQ ID NO 85
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (5)..(5)
<223> OTHER INFORMATION: amide-terminated amino acid

<400> SEQUENCE: 85

Gly Arg Lys Gly Asp
1               5

<210> SEQ ID NO 86
<211> LENGTH: 6
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated

<400> SEQUENCE: 86

Lys Leu Ala Lys Lys Leu
1               5
```

```
<210> SEQ ID NO 87
<211> LENGTH: 6
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (6)..(6)
<223> OTHER INFORMATION: amide-terminated amino acid

<400> SEQUENCE: 87

Ala Lys Lys Leu Ala Lys
1               5

<210> SEQ ID NO 88
<211> LENGTH: 6
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated

<400> SEQUENCE: 88

Ala Lys Lys Ala Leu Lys
1               5

<210> SEQ ID NO 89
<211> LENGTH: 6
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (6)..(6)
<223> OTHER INFORMATION: amide-terminated amino acid

<400> SEQUENCE: 89

Ser Thr Lys Thr Thr Lys
1               5

<210> SEQ ID NO 90
<211> LENGTH: 8
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (8)..(8)
<223> OTHER INFORMATION: amide-terminated amino acid

<400> SEQUENCE: 90

Ser Arg Val Ser Arg Arg Ser Arg
1               5
```

```
<210> SEQ ID NO 91
<211> LENGTH: 9
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (9)..(9)
<223> OTHER INFORMATION: amide-terminated amino acid

<400> SEQUENCE: 91

Leu Ala Lys Leu Ala Lys Lys Ala Phe
1               5

<210> SEQ ID NO 92
<211> LENGTH: 9
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated

<400> SEQUENCE: 92

Leu Ala Lys Lys Ala Leu Lys Ala Phe
1               5

<210> SEQ ID NO 93
<211> LENGTH: 6
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (1)..(6)
<223> OTHER INFORMATION: The amino acids at these positions are "d"
      amino acids.

<400> SEQUENCE: 93

Lys Leu Ala Lys Lys Leu
1               5

<210> SEQ ID NO 94
<211> LENGTH: 6
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (6)..(6)
<223> OTHER INFORMATION: amide-terminated amino acid

<400> SEQUENCE: 94

Thr Lys Thr Ser Lys Ser
1               5
```

<210> SEQ ID NO 95
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (5)..(5)
<223> OTHER INFORMATION: amide-terminated amino acid

<400> SEQUENCE: 95

Lys Arg Gly Asp Arg
1               5

<210> SEQ ID NO 96
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (5)..(5)
<223> OTHER INFORMATION: amide-terminated amino acid

<400> SEQUENCE: 96

Lys Ser Ser Lys Ser
1               5

<210> SEQ ID NO 97
<211> LENGTH: 4
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (4)..(4)
<223> OTHER INFORMATION: amide-terminated amino acid

<400> SEQUENCE: 97

Lys Thr Thr Lys
1

<210> SEQ ID NO 98
<211> LENGTH: 5
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (4)..(4)
<223> OTHER INFORMATION: amide-terminated amino acid
<220> FEATURE:
<221> NAME/KEY: MISC_FEATURE

```
-continued

<222> LOCATION: (5)..(5)
<223> OTHER INFORMATION: The amino acid at this position is a "d"
      amino acid.

<400> SEQUENCE: 98

Lys Lys Ala Leu Lys
1               5

<210> SEQ ID NO 99
<211> LENGTH: 6
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated

<400> SEQUENCE: 99

Leu Lys Lys Ala Leu Lys
1               5

<210> SEQ ID NO 100
<211> LENGTH: 4
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Myristoylated
<220> FEATURE:
<221> NAME/KEY: MISC_FEATURE
<222> LOCATION: (4)..(4)
<223> OTHER INFORMATION: amide-terminated amino acid

<400> SEQUENCE: 100

Lys Ala Lys Leu
1
```